United States Patent

Pak et al.

[11] Patent Number: 5,430,153
[45] Date of Patent: Jul. 4, 1995

[54] 2-QUINOLINONE DERIVATIVES

[75] Inventors: Chwang S. Pak; Eun B. Choi; Heui C. Yang; Gyu H. Yon; Ge H. Lee; Hyeon K. Lee; Sung K. Kim; Yeon S. Lee; Kwang W. Lee; Young R. Chung; Heung T. Kim, all of Daejeon, Rep. of Korea

[73] Assignee: Korea Research Institute of Chemical Technology, Daejeon, Rep. of Korea

[21] Appl. No.: 952,491
[22] PCT Filed: Apr. 3, 1992
[86] PCT No.: PCT/KR92/00010
  § 371 Date: Feb. 3, 1993
  § 102(e) Date: Feb. 3, 1993
[87] PCT Pub. No.: WO92/17452
  PCT Pub. Date: Oct. 15, 1992

[30] Foreign Application Priority Data

Apr. 3, 1991 [KR] Rep. of Korea ............... 91-5391
Apr. 3, 1991 [KR] Rep. of Korea ............... 91-5392

[51] Int. Cl.[6] ............... C07D 215/38; C07D 215/227; C07D 215/18
[52] U.S. Cl. ............... 546/155; 546/156; 546/157; 544/3; 544/107; 544/63; 544/224; 544/333
[58] Field of Search ............... 546/155, 156, 157; 514/312; 544/3, 107, 63, 224, 333

[56] References Cited

FOREIGN PATENT DOCUMENTS 55-57566 4/1980 Japan .
62-111902 5/1987 Japan .

OTHER PUBLICATIONS

H. Junjappa, "α-Oxoketene-S, S-, N, S-and N, N-Acetalja . . .", Tetrahedron Report Number 278, (1990), vol. 46, No. 16, pp. 5423–5506.
Huffman et al., "Reactions of some Acylquinolones with Diazomethane" The Journal of Organic Chemistry, vol. 34, No. 7, Jul. 1969, pp. 2183–2187.
Huffman et al., "The Furanoquinoline Alkaloids. III. An Attempted Synthesis of dl–Lunacrine and Correction of the Structure of 'Demethoxylunacrine'", Note, vol. 31, Apr. 1966, pp. 1276–1279.
Girges et al., "Synthesis of Some New 3–Substituted–4–Hydroxy–1–Methyl–Quinolin–2–One Derivatives as Potential Antibacterial and Antifungal Agents", Collection Szechoslovak Chem. Commun., vol. 53, 1988, pp. 3179–3183.

(List continued on next page.)

Primary Examiner—C. Warren Ivy
Assistant Examiner—D. Margaret M. Mach
Attorney, Agent, or Firm—Cushman Darby & Cushman

[57] ABSTRACT

The present invention relates to novel 2-quinolinone derivanves of the following general formula(I) useful in agriculture, especially as fungicides but also as insecticides and miticides.

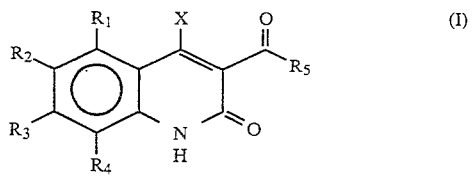

wherein,
  $R_1$, $R_2$, $R_3$ and $R_4$ are independently hydrogen, halogen, $C_1$–$C_{10}$ alkyl, branched $C_c$–$C_4$ alkyl, $C_1$–$C_3$ haloalkyl, $C_1$–$C_3$ alkoxy, $C_1$–$C_3$ haloalkoxy, $C_1$–$C_3$ alkylthio, $C_1$–$C_3$ haloallcylthio, $NO_2$, CN, alkoxy carbonyl, phenyl, substituted phenyl, phenoxy, substituted phenoxy, benzenesulfonyl, benzyi, substituted benzyl or morpholine;
  $R_5$ is $C_1$–$C_6$ alkyl, branched $C_3$–$C_6$ alkyl, $C_3$–$C_6$ cycloalkyl, phenyl, substituted phenyl, benzyl or phenylthio methyl: and
  X is $S(O)nR_6$, $OR_9$ or NAB:
wherein.
  n is 0 or 1;
  $R_6$, $R_9$, A and B are defined within the description.

4 Claims, No Drawings

OTHER PUBLICATIONS von H.-J. Gais et al., "Acetylene mit Elektronendonator-und Elektronenakzeptorgruppen", *Helvetic Chimica Acta,* vol. 52, Fasc. 8 (1969)–Nr. 263, pp. 2641–2657.

R. Gompper and W. Topfl, "Substituierte Dithiocarbonsauren und Ketenmercaptale", Chem. Ber. 95, (1962) pp. 2861–2870.

H. Junjappa, H. Ila and C. V. Asokan, "α-Oxoketene-S,S-, N,S-and N,N-Acetals: Versatile Intermediates in Organic Synthesis", Tetrahedron Report Number 278, (1990) vol. 46, No. 16, pp. 5423–5506.

Michael Kolb, "Ketene Dithioacetals in Organic Synthesis: Recent Developments", Synthesis, (1990) pp. 171–190.

R. Karl Dieter, "α-Oxo Ketone Dithioacetals and Related Compounds: Versatile Three–Carbon Synthons", Tetrahedron Report Number 202, (1986), vol. 42, No. 12, pp. 3029–3096.

Masatake Yokoyama and Tsuneo Imamoto, "Organic Reactions of Carbon Disulfide", Synthesis, (1984) pp. 797–824.

2-QUINOLINONE DERIVATIVES

BACKGROUND OF THE INVENTION

Field of the Invention

The present invention relates to novel 2-quinolinone derivatives of the following general fomula(I) useful in agriculture, especially as fungicides but also as insecticides and miticides.

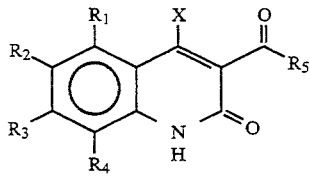

wherein, $R_1$, $R_2$, $R_3$ and $R_4$ are independently hydrogen, halogen, $C_1$-$C_{10}$ alkyl, branched $C_3$-$C_4$ alkyl, $C_1$-$C_3$ haloalkyl, $C_1$-$C_8$ alkoxy, $C_1$-$C_3$ haloalkoxy, $C_1$-$C_3$ alkylthio, $C_1$-$C_3$ haloalkylthio, $NO_2$, CN, alkoxy carbonyl, phcnyl, substituted phenyl, phenoxy, substituted phenozxy, benzenesulfonyl, benzyl, substituted benzyl or morpholine;

$R_5$ is $C_1$-$C_6$ alkyl, branched $C_3$-$C_6$ alkyl. $C_3$-$C_6$ cycloalkyl, phenyl, substituted phenyl, benzyl or phenylthio methyl; and X is $S(O)nR_6$, $OR_9$ or NAB:

wherein, n is 0 or 1:

$R_6$ is $R_7$ or $R_8$, and then $R_7$ is $C_1$-$C_6$ alkyl, branched $C_3$-$C_6$ alkyl, $C_1$-$C_3$ haloalkyl, benzyl or substituted benzyl, and $R_8$ is phenyl, substituted phenyl, benzyl or substituted benzyl;

$R_9$ is $C_2$-$C_5$ alkyl, branched $C_3$-$C_4$ alkyl, $C_5$-$C_6$ cycloalkyl, phenyl or substituted phenyl;

A and B are combined together to fonn a saturated or unsaturated 5 or 6-membered cyclic ring or fused ring, optionally including a hetero atom selected from O or N, or optionally substituted with $C_1$-$C_3$ alkyl or carbocyclic ring including N atom, or one of A and B is H and the other is $R_{10}$ or Z—Ar; and then, $R_{10}$ is saturated or unsaturated $C_1$-$C_{10}$ alkyl, branched $C_3$-$C_8$ alkyl or $C_3$-$C_6$ cycloalkyl optionally including a hetero atom selected from O, S or N or optionally substituted with $C_1$-$C_3$ alkyl or alkoxycarbonyl, $C_1$-$C_3$ haloalkyl, alkoxyalkyl, alkoxycarbonylalkyl, phenyl, substituted phenyl, pyridyl, substituted pyridyl, pyrimidyl, or substituted pyrimidyl;

Z is $C_1$-$C_4$ alkyl chain, optionally containing cyclopropylene ring, or optionally substituted with $C_1$-$C_3$ alkyl, $C_1$-$C_3$ alkoxy, $C_1$-$C_3$ hydroxyalkyl or or phenyl; and Ar is $C_3$-$C_6$ cycloalkyl, optionally including a nitrogen atom, or pyridyl, substituted pyridyl, or a phenyl group of the following formula (II)

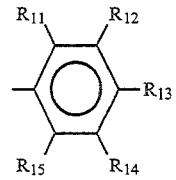

wherein, $R_{11}$, $R_{12}$, $R_{13}$, $R_{14}$ and $R_{15}$ are independently H, halogen, $C_1$-$C_6$ alkyl, branched $C_3$-$C_4$ alkyl, $C_1$-$C_4$ haloalkyl, $C_1$-$C_4$ alkoxy, phenyl, phenoxy, phenylthio, CN, $NO_2$, $NH_2$, or $SO_2NH_2$.

Description of the Prior Art

There is an acute need for new fungicities, insecticides, and miticides, because target pathogens are rapidly developing resistance to currently used pesticides. The development of resistance to some of the fungicides in current use, such as the triazoles, the benzimidazoles, the acylalanines, and the organophosphates and the insecticides, such as the carbamates, the organophosphates, and the pyrethroids, is well known. Therefore a need exists for new fungitides, insecticides, and miticides.

SUMMARY OF THE INVENTION

The present invention relates to novel 2-quinolinone derivatives having the above general formula(I), which have fungicidal and insecticidal activity.

DETAILED DESCRIPTION OF THE INVENTION

The compounds of the general formula(I) according to the present invention can be prepared by reactions as described herein below.

The compounds(Ia) of general formula(I) wherein X is $SR_6$, and then $R_6$ is $R_7$, can be made by thermally cyclizing compounds of following formula(III), and the compounds(Ib) of general formula(I) wherein X is $SOR_6$, and then $R_6$ is $R_7$, may be prepared by oxidizing the corresponding compounds(Ia) using a conventional oxidation procedure.

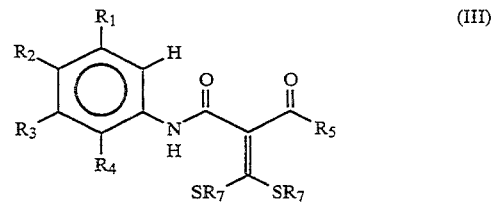

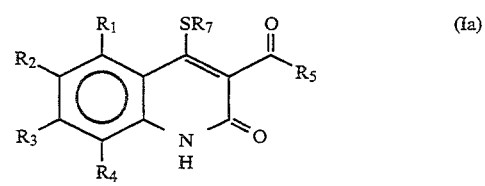

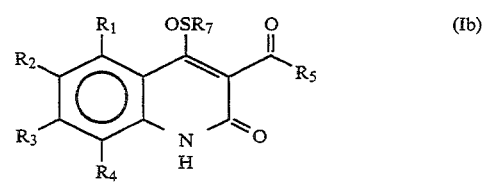

wherein, $R_1$, $R_2$, $R_3$, $R_4$, $R_5$ and $R_7$ are as previously defined.

The above reaction may be carried out without solvent or under the presence of solvent, for example, hydrocarbon solvents such as paraffin oil, benzenes such as xylene and dichlorobenzene, amides such as dimethyl formamide and dimethyl acetamide, anilines such as N,N-dimethylaniline and N,N-diethyl aniline, ethers such as diphenyl ether, or a mixture of them.

The cyclizing reaction is carried out at 140°~250° C., preferably 160°~200° C. If the temperature is lower than 140° C., the reaction rate is very slow, and ff higher than 250° C., it is attended with the severe evolution of mercaptan($R_7SH$) as a by-product.

Alteratively, the compounds($Ia'$) of general formula(I) wherein X is $SR_6$, and then $R_6$ is $R_8$, can be manufactured by reacting the compounds of above formula(Ib) with thiol of following formula(IV), and the compounds($Ib'$) wherein X is $SOR_6$, and then $R_6$ is $R_8$, can be prepared by oxidizing the corresponding compounds($Ia'$) using a conventional oxidation procedure.

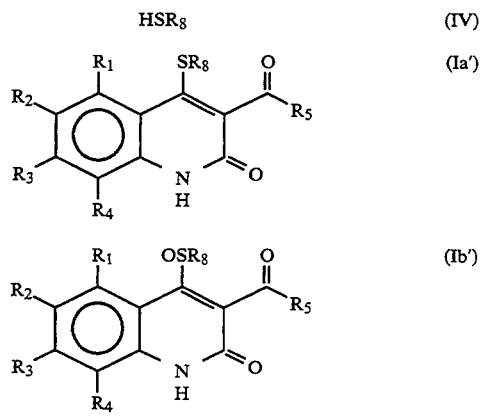

wherein, $R_1$, $R_2$, $R_3$, $R_4$, $R_5$ and $R_8$ are as previously defined.

The compounds of above formula($Ia'$) can be prepared by the substitution reaction heating 4-alkylsulfoxyquinolinone of the above formula(Ib) and thiophenol derivative of the above formula(IV) without solvent or under the presence of solvent, and then the solvent as the above, e.g. hydrocarbons, benzenes, amides, anilines, ethers, or their mixture, may be used.

The substitution reaction is carried out at 100°~250° C., preferably 160°~200° C. If the temperature is lower than 100° C., the reacting rate is very slow, and if higher than 250° C., the yields are very low.

The compounds(when n in X of formula(I) is 1) of the formula(Ib) and ($Ib'$) can be prepared by oxidation of the compounds(when n in X of formula(I) is 0) of the formula(Ia) and ($Ia'$) using a conventional oxidants, for example, organic or inorganic peroxy compounds such as hydrogen peroxide, potassium peroxymonosulfate, tertiary butyl hydroperoxide, m-chloro peroxybenzoic acid, peroxyacetic acid, and magnesium monoperoxyphthalate.

And then, solvent may be used as followings; water; hydrocarbon halide such as dichloromethane, chloroform, carbon tetrachloride, and chlorobenzene; aliphatic acid such as acetic acid and propionic acid; or alcohols such as methyl alcohol, ethyl alcohol, etc.

The reaction may be carried out at 0°~130° C., preferably 20°~60° C., and then if the temperature is lower than 0° C., the reaction rate is very slow, and if higher than 130° C., the used solvent may be boiled over.

The amount of used oxidant may be usefully 1.2 fold or more with the used compound of the formula(Ia) or ($Ia'$), but it is not limited specially.

The quinolinone derivatives of the formula(Ia) and ($Ib'$) and sulfoxy-2-quinolinone derivatives may be optionally recrystallized or purified by chromatography.

The compounds(Ic) of general formula(I) wherein X is $OR_9$ and then $R_9$ is methyl can be prepared by the known process described in J. Org. Chem. Vol. 31, P1276–1278(1966) or J. Org. Chem. Vol. 34, P2183–2187(1969) by J. W. Huffman and J. H. Cecil. Especially, 3-isobutyryl-4-methoxy-(2H)quinolinone, 3-isobutyryl- 4,8-dimethoxy-2( 1H)-quinolinone, 3-isovaleryl-4-methoxy-2(1H)-quinolinone or 3-isovaleryl-4,8-dimethoxy-2(1H)-quinolinone were prepared in 14~18% yields by reacting the corresponding 3-acyl-4-hydroxy-2( 1H)-quinolinone with diazomethane, and separation of the resulted mixture of 2(1H)-quinolinone, 1-methyl-2(1H)-quinolinone and other products as using liquid chromatography.

In this invention, the compounds(Ic) of general formula(I) wherein X is $OR_9$ were made by condensing the compounds of formula(Ib) with an alcohol of the formula(V).

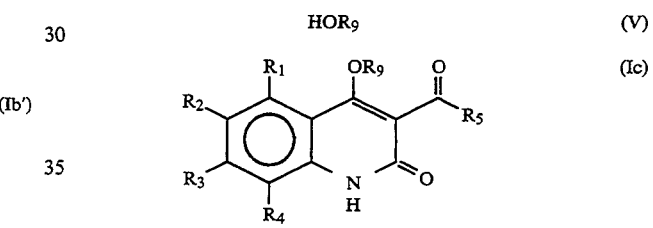

wherein, $R_1$, $R_2$, $R_3$, $R_4$, $R_5$ and $R_9$ are as previously defined.

Also, the above compound(Ic) may be prepared by substitution of alcohols($R_9OH$) under heating without solvent or under the presence of a solvent, or directly using alcohol as a solvent, and then the base may be used or not.

The used solvent may be, excepting alcohol used as a reactant, dimethyl formamide, acetonitrile, dioxane, benzene, toluene, xylene, tetrahydrofuran, hexane, heptane, or a mixture of them. The base may be, for example, pyridine, triethylamine, N,N-dialkylaniline, alkalimetal hydroxide, alkalimetal carbonate, metal hydride, etc.

The substitution reaction is carried out at boiling point of solvent or between room temperature and 200° C., preferably at 50°~120° C.

The compounds(Id) of general formula(I) wherein X is NAB and then NAB is $NMe_2$ can be prepared by the known process described in Helv. Chim. Acta., Vol. 52, P 264~2657(1969) by H. J. Gais, K. Hafiner and M. Neuenschwander. Especially, 3-acetyl-4,8- (dimethylamino)- 2(1H)-quinolinone may be obtained by reaction of phenylisocyanate and 1-dimethytamino-3-oxo-1-butylene according to [4+2]cycloaddition.

In this invention, the compounds(Id) of general formula(I) wherein X is NAB were prepared by condensing the compounds of formula(Ib) with the amines of the formula(VI)

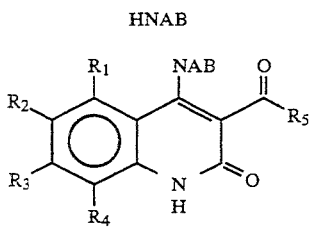

(Id)

wherein, $R_1$, $R_2$, $R_3$, $R_4$, $R_5$, A and B are as previously defined.

The above compound(Id) a be prepared by reacting 4-alkylsulfoxy-2-quinolinone of the above formula(Ib) with an amine compound of the following formula(VI) under the presence of inert solvent.

When the amine compound of formula(VI) is acid salt, an acid remover for example, trialkylamines (such as triethylamine), potassium carbonate, inorganic base (such as sodium hydroxide), may be used, as adding 1~2 equivalents, and thereafter acid adding salt of amine compound is added.

An inert solvent used in the present invention may be, for example, ethers such as diethylether, diisopropyl ether, tetrahydrofuran, dioxane, diphenylether, etc.; hydrocarbons such as benzene, toluene, xylene, ligroine, etc.; hydrocarbon halides such as dichloroethane, chloroform, carbon tetrachloride, etc.; esters such as ethyl acetate, ethyl propionate, etc.; chlorobenzenes such as monochlorobenzene, dichlorobenzene, etc.; aprotic polar solvents such as N,N-dimethylformamide, dimethyl sulfoxide, etc., but the above reaction may be carried out without solvent.

According to the present invention, pyridine or trialkylamine may be used as two purposes of a base and a solvent. The reaction can be carried out at 0°~260° C., preferably between room temperature and boling point of the solvent, and then the reacting time is preferable of 0.5~8 hr but it is affected by the reaction temperature.

As a result of the reaction, when the amine compound of formula(VI) being not acid adding salt is used, the crude product is obtained by evaporating the solvent under the reduced pressure.

But, when the amine compound of formula(VI) being acid adding salt is used, the crude product may be obtained by following process; the solvent is evaporated under the reduced pressure; water is added to dissolve the salts; the resulting mixture is extracted with water-insoluble organic solvent such as methylenechloride, chloroform, ethyl acetate, etc.; and the organic layer is evaporated under the reduced pressure to afford the crude product.

The obtained 2-quinolinone derivatives of formula(Id) may be purified by column chromatography or recrystallized by the following solvent; alcohol solvent such as methanol, ethanol, etc.; ester of organic acid such as ethyl acetate, methyl acetate, etc.; hydrocarbon solvent such as pentane, hexane, etc.; ether such as ethylether, tetrahydrofuran, etc.

On the other hand, the starting material used in the present invention, ketene dithio acetal α-anilide of the formula(IH), can be prepared from β-ketoanilide by the following reaction process

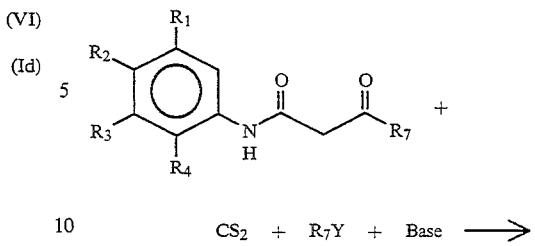

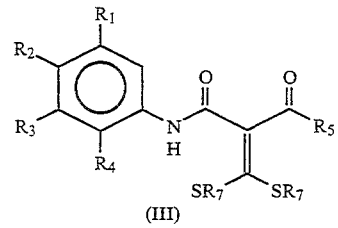

wherein, $R_1$, $R_2$, $R_3$, $R_4$, $R_5$ and $R_7$ is respectively as the above defined, Y is chlorine, bromine, iodine, or alkyl or arylsulfonate.

The compounds according to the present invention have highly curative and protective fung icidal activity for plant germs of widely spectrum as followings; for example, rice blast (*Piricularia oryzae*), rice sheath blight (*Rhizoctonia solani*), cucumber gray mold (*Botrytis cinerea*), cucumber powdery mildew (*Sphaerotheca fuliginea*), cucumber downy mildew (*Pseudoperonospora cubensis*), grape downy mildew (*Plasmopora viticola*), tomato late blight (*Phytophthora infestans*), rice brown spot (*Cochliobolus miyabeanus*), peanut brown leaf spot (*Cercospora arachidicola*), barley powdery mildew (*Erysiphe graminis*), wheat leaf rust (*Puccinia recondita*), wheat stem rust (*Puccinis graminis*), and wheat eye spot (*Pseudocercosporella herpotrichoides*). Also, the compounds according to the present invention have highly insecticidal activity for noxious insects, for example, house fly, mosquito, cockroach and agricultral insects, for example, Hemiptera such as small brown plant hopper (*Laodephax striatellus Fallen*), brown plant hopper (*Nilaparvata lugens Stail*), white-backed rice plant hopper (*Sogatella furcifera Horvath*), green rice leaf hopper (*Nephotettix cincticeps Uhler*), greenhouse white fly (*Trialeurodes vaporariorum Westwood*), and green peach aphid (*Myzus persicae Sulzer*); Lepidoptera such as apple leafminer (*Phyllonorycter ringoniella Matsumura*), diamond-back moth (*Plutella xylostella Curtis*), rice armyworm (*Pseuclaletia separata Walker*), cabbage armyworm (*Mamestra brassicae Linnaeus*), tobacco cutworm (*Spodoptera litura Fablicius*), and common cabbage worm(*Pieris rapae Linnaeus*); Coleoptera such as rice leaf beetle (*Oulema oryzae Kuiwayarna*), and riceplant weevil rice curculio (*Echinocnemus squameus Billbery*).

Useful formulations of the compounds of formula(I) can be prepared by mixing the compounds of active ingredient of about 0.01~90 weight % with proper solid or liquid carrier and supporters such as surfactant, diluent, spreader, synergist, adhesive, dispersant, etc.

The used solid carrier may be usually chosen from among the attapulgite clays, the montmorillonite clays, the diatomaceous earths, or the purified silicates, and liquid carrier may be water, alcohol, methanol, ethanol, acetone, dimethylformamide, ether, benzene, xylene, toluene, naphtha, etc.

Suffactant may be nonionic suffactant(e.g., polyoxy ethylene alkylphenylether and poly oxyethylene fatty acid ester), artionic suffactant(alkyl benzenesulfonic acid, lignine sulfonate and dinaphthalene methane sulfonate), etc. Polyvinylalcohol, CMC, gum arabic, etc. may be used as adhesive.

The fungicidal and insecticidal compositions using the compounds of the present invention may be manufactured as formulation such as powder, wettable powder, granules, emulsifiable concentrates, suspensions, solution, fumigant, gas phase, etc., and thekr fonnulations were used in earth, agriculural products, seedling, seeds, etc.

For example, emulsifiable concentrates or solution may be prepaxed by uniformly dissolving the compound of formula(I) with hydrocarbon, acetone or alcohol and surfactant.

Wettable powders, which may be compacted to form water dispersible granules, comprise an intimate mixture of the active compound, inert carder and surfactants.

The combinations including the compounds according to the present invention may be used by mixing with agricultural chemicals such as insecticides, fungicides, herbicides, plant growth regulants, miticides, etc.

Especially, since the known fungicides have resistance, the compounds of formula(I) of more than 1 weight % may be used with the known fungicides including following compounds;

1) N-substituted azoles, for example, prochloraz, triademefon, and flusilazol;
2) pyrimidines, such as fenarimol and nuarimol;
3) morpholines, such as fenpropimorph and tridemorph;
4) piperazines, such as triforine;
5) pyridines, such as pyrifenox;
6) dithiocarbamates, such as maneb and mancozeb;
7) phthalimides, such as captafol;
8) isophthalonitriles, such as chlorothalonil;
9) dicarboximides, such as iprodione;
10) benzimidazoles, such as benomyl and carbendazim;
11) 2-aminopyrimidines, such as ethirimol;
12) carboxamides, such as carboxin; and
13) dinitrophenols, such as dinocap.

The fungicide combinations of the invention contain at least 1%, generally 20~80% by weight of a compound of formula (1).

The compounds of said formula(I) according to the present invention specify as the following Tables 1~4;

TABLE 1

4-alkyl or arylthio-2-quinolinone(I-a, I-a') and 4-alkyl or arylsulfoxy-2-quinolinone(I-b, I-b')

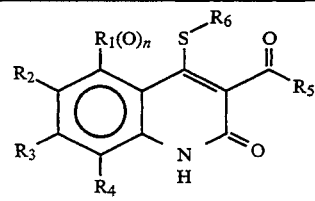

| Comp. No. | $R_1$ | $R_2$ | $R_3$ | $R_4$ | $R_5$ | $R_6$ | n | m.p. (°C.) |
|---|---|---|---|---|---|---|---|---|
| 1 | H | H | H | H | $CH_3$ | $CH_3$ | 0 | 226–231 |
| 2 | " | " | $OCH_3$ | " | " | " | " | 194–199 |
| 3 | " | " | H | Cl | " | " | " | 135–137 |
| 4 | Cl | " | " | Cl | " | " | " | 171–175 |
| 5 | H | $OCH_3$ | " | H | " | " | " | 232–233 |
| 6 | " | H | F | " | " | " | " | 225–227 |
| 7 | " | F | H | " | " | " | " | 233–235 |
| 8 | " | H | " | F | " | " | " | 139–141 |
| 9 | " | " | " | Cl | $n\text{-}C_3H_7$ | " | " | 110–112 |
| 10 | " | " | " | " | $C_2H_5$ | " | " | 130–131 |
| 11 | " | " | " | $CH_3$ | $CH_3$ | " | " | 93–94 |
| 12 | " | " | " | Cl | $C_6H_5$ | " | " | 199–202 |
| 13 | " | Cl | " | $CF_3$ | $CH_3$ | " | " | 118–121 |
| 14 | " | H | " | H | $C_6H_5$ | " | " | 265–268 |
| 15 | " | " | " | F | $CH_3$ | 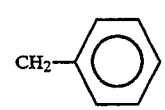 | " | 109–111 |
| 16 | H | H | H | $CO_2CH_3$ | $CH_3$ | $CH_3$ | 0 | 233–234 |
| 17 | " | Cl | " | H | " | " | " | 197–198 |
| 18 | " | H | " | $NO_2$ | " | " | " | 184–185 |
| 19 | $NO_2$ | " | " | Cl | " | " | " | 201–203 |
| 20 | H | $NO_2$ | " | H | " | " | " | 222–226 |
| 21 | " | Cl | $NO_2$ | H | " | " | " | 281–283 |
| 22 | " | H | H | CN | " | " | " | 171–173 |
| 23 | " | Cl | " | $CF_3$ | $CH_3$ | 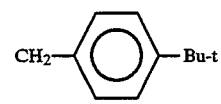 | " | 110–113 |
| 24 | " | t-Bu | " | H | " | $CH_3$ | " | 154–156 |
| 25 | " | H | " | $SO_2C_6H_5$ | " | " | " | 211–213 |
| 26 | $NO_2$ | " | " | F | " | " | " | >260 |

TABLE 1-continued 4-alkyl or arylthio-2-quinolinone(I-a, I-a') and 4-alkyl or arylsulfoxy-2-quinolinone(I-b, I-b')

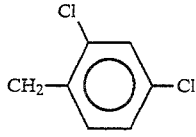

| Comp. No. | R₁ | R₂ | R₃ | R₄ | R₅ | R₆ | n | m.p. (°C.) |
|---|---|---|---|---|---|---|---|---|
| 27 | Cl | Cl | Cl | Cl | " | " | " | 188–191 |
| 28 | H | CF₃ | H | H | " | " | " | 151–153 |
| 29 | " | H | " | CF₃ | " | " | " | 98–99 |
| 30 | " | Br | " | " | " | " | " | 139–141 |
| 31 | " | H | " | SCF₃ | CClFH | " | " | 127–129 |
| 32 | " | OC₅H₁₁-n | " | H | " | " | " | 134–137 |
| 33 | " | F | " | CF₃ | " | " | " | 138–140 |
| 34 | " | H | F | " | " | " | " | 164–166 |
| 35 | " | Br | CF₃ | H | " | " | " | 138–140 |
| 36 | " | Cl | " | " | " | " | " | 149–151 |
| 37 | " | n-C₆H₁₃ | H | " | " | " | " | 94–98 |
| 38 | " | F | F | F | " | " | " | 132–134 |
| 39 | " | Cl | H | CF₃ | " |  | " | 143–144 |
| 40 | " | F | Cl | H | " | CH₃ | " | 141–143 |
| 41 | CF₃ | H | H | Cl | " | " | " | 206–208 |
| 42 | H | Cl | H | CH₃ | CH₃ | CH₃ | 0 | 164–166 |
| 43 | " | H | " | C₂H₅ | " | " | " | 87–88 |
| 44 | " | " | " | " | " | 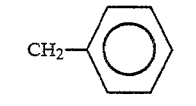 | " | 116–117 |
| 45 | " | CF₃ | Cl | H | " | CH₃ | " | 149–151 |
| 46 | " | H | " | Cl | " | " | " | 143–144 |
| 47 | " | t-Bu | H | H | " | 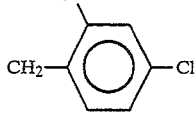 | " | 118–120 |
| 48 | " | H | " | CN | " | 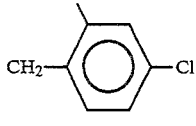 | " | 115–116 |
| 49 | " | CF₃ | " | NO₂ | " | CH₃ | " | 156–157 |
| 50 | H | Cl | Cl | H | CH₃ | CH₃ | " | 150–152 |
| 51 | Cl | " | H | " | " | " | " | 223–225 |
| 52 | H | H | CF₃ | " | " | " | " | 135–138 |
| 53 | " | Cl | H | Cl | " | 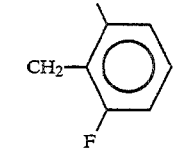 | " | 215–217 |
| 54 | " | " | " | CF₃ | " |  | " | 179–181 |

TABLE 1-continued 4-alkyl or arylthio-2-quinolinone(I-a, I-a') and 4-alkyl or arylsulfoxy-2-quinolinone(I-b, I-b')

| Comp. No. | R₁ | R₂ | R₃ | R₄ | R₅ | R₆ | n | m.p. (°C.) |
|---|---|---|---|---|---|---|---|---|
| 55 | Cl | H | " | Cl | " | CH₂-(2,4-diClC₆H₃) | " | 184–185 |
| 56 | H | Cl | " | " | " | CH₂-C₆H₅ | " | 101–102 |
| 57 | " | " | " | CH₃ | " | CH₂-(2,4-diClC₆H₃) | " | 162–163 |
| 58 | " | " | " | " | " | CH₂-(3-CF₃C₆H₄) | " | 158–160 |
| 59 | Cl | H | " | " | " | CH₃ | " | 164–165 |
| 60 | CH₃ | " | CH₃ | H | " | " | " | 151–153 |
| 61 | Cl | " | H | Cl | " | n-C₄H₉ | " | 105–106 |
| 62 | H | " | " | i-C₃H₇ | " | CH₃ | " | 101–102 |
| 63 | Cl | " | Cl | H | " | " | " | 165–166 |
| 64 | H | " | H | CF₃ | " | n-C₄H₉ | " | 91–93 |
| 65 | " | " | " | C₆H₅ | " | CH₃ | " | 131–132 |
| 66 | " | " | " | " | " | n-C₄H₉ | " | 84–87 |
| 67 | " | " | " | " | " | CH₂-(2,4-diClC₆H₃) | " | 123–126 |
| 68 | H | H | H | C₆H₅ | CH₃ | CH₂-(3-CF₃C₆H₄) | 0 | 82–83 |
| 69 | CH₃ | " | " | Cl | " | CH₃ | " | 159–161 |
| 70 | H | CH₃ | " | CH₃ | " | CH₂-(2,4-diClC₆H₃) | " | 138–139 |
| 71 | Cl | H | " | Cl | " | CH₂-(3-CF₃C₆H₄) | " | 155–156 |

TABLE 1-continued 4-alkyl or arylthio-2-quinolinone(I-a, I-a') and 4-alkyl or arylsulfoxy-2-quinolinone(I-b, I-b')

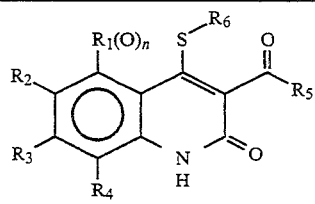

| Comp. No. | $R_1$ | $R_2$ | $R_3$ | $R_4$ | $R_5$ | $R_6$ | n | m.p. (°C.) |
|---|---|---|---|---|---|---|---|---|
| 72 | H | H | H | i-$C_3H_7$ | $CH_3$ | $CH_2$-(2,4-Cl₂-C₆H₃) | " | 117–119 |
| 73 | " | " | " | " | " | n-$C_4H_9$ | " | 44–45 |
| 74 | " | " | " | $CH_2C_6H_5$ | " | $CH_3$ | " | 135–137 |
| 75 | " | Cl | " | $CF_3$ | " | $C_2H_5$ | " | 87–89 |
| 76 | " | H | " | n-$C_3H_7$ | " | $CH_3$ | " | 73–74 |
| 77 | " | " | Cl | $CH_3$ | " | $CH_3$ | " | 132–135 |
| 78 | " | Cl | H | $CF_3$ | " | n-$C_6H_{13}$ | " | 66–68 |
| 79 | " | $CH_3$ | Cl | H | " | $CH_3$ | " | 143–145 |
| 80 | Cl | " | H | " | " | " | " | 156–158 |
| 81 | H | H | " | $CH_2C_6H_5$ | " | n-$C_4H_9$ | " | 80–81 |
| 82 | " | " | " | " | " | i-$C_5H_{11}$ | " | 66–67 |
| 83 | " | Cl | " | F | " | $CH_3$ | " | 153–156 |
| 84 | " | $NO_2$ | " | Cl | " | " | " | 197–198 |
| 85 | $CH_3$ | H | " | " | " | " | " | 161–162 |
| 86 | H | F | " | " | " | " | " | 146–147 |
| 87 | $CF_3$ | H | " | $OCH_3$ | " | " | " | 259–261 |
| 88 | H | $OCH_3$ | " | $NO_2$ | " | " | " | 175–179 |
| 89 | " | H | Cl | Cl | " | $C_2H_5$ | " | 118–120 |
| 90 | " | " | H | $CH_3$ | " | $CH_3$ | 1 | 204–206 |
| 91 | " | " | " | Cl | " | " | " | 219–220 |
| 92 | " | $OCH_3$ | " | H | " | " | " | 220 |
| 93 | Cl | H | " | Cl | " | " | " | 240–242 |
| 94 | H | Cl | H | H | $CH_3$ | $CH_3$ | 1 | 235–238 |
| 95 | " | H | " | Cl | $C_6H_5$ | " | " | 221–223 |
| 96 | " | F | " | H | $CH_3$ | " | " | 242–244 |
| 97 | " | H | " | F | " | " | " | 190–193 |
| 98 | " | Cl | " | $CF_3$ | " | " | " | 196–198 |
| 99 | " | H | " | H | $C_6H_5$ | " | " | 239–241 |
| 100 | " | H | H | F | " | $CH_2C_6H_5$ | " | 218–220 |
| 101 | " | H | H | $CO_2CH_3$ | $CH_3$ | $CH_3$ | " | 232–234 |
| 102 | " | " | " | $CF_3$ | " | " | " | 211–213 |
| 103 | " | " | " | $SO_2C_6H_5$ | " | " | " | 209–211 |
| 104 | " | " | " | CN | " | " | " | 224–226 |
| 105 | $NO_2$ | " | " | F | " | " | " | 246–248 |
| 106 | $CF_3$ | " | " | Cl | " | " | " | 233–235 |
| 107 | H | F | Cl | H | " | " | " | 245–247 |
| 108 | " | Cl | H | Cl | " | " | " | 214–216 |
| 109 | $NO_2$ | H | " | " | " | " | " | 247–249 |
| 110 | H | Cl | " | $CH_3$ | " | " | " | 220–222 |
| 111 | " | H | " | $C_2H_5$ | " | " | " | 210–211 |
| 112 | " | " | Cl | Cl | " | " | " | 200–202 |
| 113 | " | $CF_3$ | H | $NO_2$ | " | " | " | 164–167 |
| 114 | " | H | $CF_3$ | H | " | " | " | 203–207 |
| 115 | " | Cl | H | $CF_3$ | " | $CH_2$-(2,4-Cl₂-C₆H₃) | " | 198–199 |
| 116 | Cl | H | " | Cl | " | " | " | 177–180 |
| 117 | H | $CF_3$ | " | H | " | $CH_3$ | " | 228–230 |

TABLE 1-continued 4-alkyl or arylthio-2-quinolinone(I-a, I-a′) and 4-alkyl or arylsulfoxy-2-quinolinone(I-b, I-b′)

| Comp. No. | $R_1$ | $R_2$ | $R_3$ | $R_4$ | $R_5$ | $R_6$ | n | m.p. (°C.) |
|---|---|---|---|---|---|---|---|---|
| 118 | ″ | Cl | ″ | $CH_3$ | ″ | 2,4-dichlorobenzyl ($CH_2$-C$_6$H$_3$Cl$_2$) | ″ | 202–203 |
| 119 | ″ | ″ | ″ | ″ | ″ | 3-(trifluoromethyl)benzyl ($CH_2$-C$_6$H$_4$CF$_3$) | ″ | 164–169 |
| 120 | Cl | H | H | $CH_3$ | $CH_3$ | $CH_3$ | 1 | 243–244 |
| 121 | $CH_3$ | ″ | $CH_3$ | H | ″ | ″ | ″ | 229–231 |
| 122 | Cl | ″ | H | Cl | ″ | n-$C_4H_9$ | ″ | 172–173 |
| 123 | Cl | ″ | Cl | H | ″ | ″ | ″ | 211–213 |
| 124 | Cl | ″ | Cl | H | ″ | ″ | ″ | 250–252 |
| 125 | $CF_3$ | ″ | $CF_3$ | ″ | ″ | ″ | ″ | 230–233 |
| 126 | H | ″ | H | $C_6H_5$ | $CH_3$ | $CH_3$ | ″ | 267–270 |
| 127 | ″ | Cl | ″ | $CF_3$ | ″ | n-$C_4H_9$ | ″ | 123–125 |
| 128 | $NO_2$ | H | ″ | $OCH_3$ | ″ | $CH_3$ | ″ | >260 |
| 129 | H | ″ | ″ | $C_6H_5$ | ″ | n-$C_4H_9$ | ″ | 147–150 |
| 130 | ″ | ″ | ″ | ″ | ″ | 3-(trifluoromethyl)benzyl ($CH_2$-C$_6$H$_4$CF$_3$) | ″ | 151–154 |
| 131 | ″ | ″ | ″ | ″ | ″ | 2,4-dichlorobenzyl ($CH_2$-C$_6$H$_3$Cl$_2$) | ″ | 209–211 |
| 132 | ″ | ″ | ″ | i-$C_3H_7$ | ″ | n-$C_4H_9$ | ″ | 111–112 |
| 133 | ″ | ″ | ″ | ″ | ″ | 2,4-dichlorobenzyl ($CH_2$-C$_6$H$_3$Cl$_2$) | ″ | 125–130 |
| 134 | ″ | ″ | ″ | $CH_2C_6H_5$ | ″ | $CH_3$ | ″ | 145–147 |
| 135 | ″ | ″ | ″ | n-$C_3H_7$ | ″ | ″ | ″ | 186–189 |
| 136 | ″ | $CH_3$ | ″ | Cl | ″ | ″ | ″ | 216–217 |
| 137 | ″ | H | Cl | $CH_3$ | ″ | ″ | ″ | 194–196 |
| 138 | ″ | Cl | H | $CF_3$ | ″ | $C_2H_5$ | ″ | 139–142 |
| 139 | ″ | ″ | ″ | ″ | ″ | n-$C_6H_{13}$ | ″ | 98–100 |
| 140 | ″ | $CH_3$ | Cl | H | ″ | $CH_3$ | ″ | 253–255 |
| 141 | Cl | ″ | H | ″ | ″ | ″ | ″ | 222–223 |
| 142 | H | H | ″ | $CH_2C_6H_5$ | ″ | i-$C_5H_{11}$ | ″ | 135–136 |
| 143 | ″ | ″ | ″ | ″ | ″ | n-$C_4H_9$ | ″ | 124–125 |
| 144 | ″ | Cl | ″ | F | ″ | $CH_3$ | ″ | 217–218 |
| 145 | ″ | $NO_2$ | ″ | Cl | ″ | ″ | ″ | 190–192 |
| 146 | $CH_3$ | H | H | Cl | $CH_3$ | $CH_3$ | 1 | 187–188 |
| 147 | H | F | ″ | ″ | ″ | ″ | ″ | 220–221 |
| 148 | $CF_3$ | H | ″ | $OCH_3$ | ″ | ″ | ″ | 201–202 |
| 149 | H | $OCH_3$ | H | $OCH_3$ | $CH_3$ | $CH_3$ | 0 | 178–180 |
| 150 | ″ | ″ | ″ | ″ | ″ | ″ | 1 | 231–232 |
| 151 | ″ | H | Cl | Cl | ″ | $C_3H_7$ | 0 | 93–95 |
| 152 | ″ | ″ | ″ | ″ | ″ | ″ | 1 | 130–132 |
| 153 | ″ | F | F | F | ″ | $CH_3$ | ″ | 184–186 |

TABLE 1-continued 4-alkyl or arylthio-2-quinolinone(I-a, I-a') and 4-alkyl or arylsulfoxy-2-quinolinone(I-b, I-b')

| Comp. No. | R₁ | R₂ | R₃ | R₄ | R₅ | R₆ | n | m.p. (°C.) |
|---|---|---|---|---|---|---|---|---|
| 154 | " | n-C₆H₁₃ | H | H | " | " | " | 152–154 |
| 155 | " | Cl | CF₃ | " | " | " | " | 265–267 |
| 156 | " | H | F | CF₃ | " | " | " | 247–250 |
| 157 | " | F | H | CF₃ | " | " | " | 202–204 |
| 158 | " | H | Cl | Cl | " | C₂H₅ | " | 143–146 |
| 159 | " | " | " | " | " | sec-C₄H₉ | 0 | 78–80 |
| 160 | " | Cl | NO₂ | HY | " | CH₃ | " | 281–283 |
| 161 | " | " | " | " | " | " | 1 | 253–255 |
| 162 | " | H | Cl | Cl | " | sec-C₄H₉ | 0 | 165–168 |
| 163 | " | [N-morpholino] | H | H | " | CH₃ | " | 208–210 |
| 164 | " | " | " | " | " | " | 1 | 210–213 |
| 165 | Cl | Cl | " | Cl | " | " | 0 | 181–183 |
| 166 | " | " | " | " | " | " | 1 | 267–270 |
| 167 | H | " | Cl | " | " | " | 0 | — |
| 168 | " | " | " | " | " | " | 1 | 183–184 |
| 169 | Cl | " | " | H | " | " | 0 | 264–266 |
| 170 | " | " | " | " | " | " | 1 | — |
| 171 | " | H | H | NO₂ | " | " | 1 | 202–204 |
| 172 | Cl | H | H | NO₂ | CH₃ | CH₃ | 0 | 197–199 |
| 173 | H | CH₃ | " | F | " | " | " | 134–135 |
| 174 | " | " | " | " | " | " | 1 | 233–235 |
| 175 | " | F | " | CH₃ | " | " | 0 | 160–161 |
| 176 | " | " | " | " | " | " | 1 | 201–202 |
| 177 | " | H | " | OC₆H₅ | " | " | 0 | 152–153 |
| 178 | " | " | " | " | " | " | 1 | 213–214 |
| 179 | " | OCF₃ | " | H | " | " | 0 | 167–168 |
| 180 | " | " | " | " | " | " | 1 | 248–251 |
| 181 | " | Cl | " | CF₃ | " | 4-Cl-C₆H₄ | " | 187–188 |
| 182 | Cl | H | " | Cl | " | " | 0 | 217–218 |
| 183 | H | Cl | " | CF₃ | " | " | " | 155–157 |
| 184 | Cl | H | " | Cl | " | " | 1 | 248–250 |
| 185 | H | Cl | " | CF₃ | " | 4-F-C₆H₄ | 0 | 244–245 |
| 186 | " | " | " | " | " | C₆H₅ | " | 191–192 |
| 187 | " | " | " | " | " | " | 1 | 156–157 |
| 188 | " | H | Cl | Cl | CH₃ | 4-Cl-C₆H₄ | 0 | 225–226 |
| 189 | " | Cl | H | CF₃ | C₂H₅ | CH₃ | " | 101–102 |
| 190 | " | " | " | " | " | " | 1 | 197–198 |
| 191 | " | H | " | Br | CH₃ | " | 0 | 167–168 |
| 192 | " | " | Cl | Cl | C₂H₅ | " | " | 150–151 |

TABLE 1-continued 4-alkyl or arylthio-2-quinolinone(I-a, I-a') and 4-alkyl or arylsulfoxy-2-quinolinone(I-b, I-b')

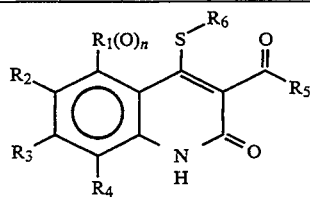

| Comp. No. | R₁ | R₂ | R₃ | R₄ | R₅ | R₆ | n | m.p. (°C.) |
|---|---|---|---|---|---|---|---|---|
| 193 | " | " | " | " | CH₃ | CH₂CF₃ | " | 160–161 |
| 194 | " | Cl | H | CF₃ | " | " | " | 103–104 |
| 195 | " | " | " | " | n-C₃H₇ | CH₃ | " | 112–113 |
| 196 | " | H | Cl | Cl | C₂H₅ | " | 1 | 204–205 |
| 197 | " | Cl | H | CF₃ | ▷ | " | 0 | 129–130 |
| 198 | H | Cl | H | CH₃ | n-C₃H₇ | CH₃ | 1 | 160–161 |
| 199 | " | " | " | " | ▷ | " | " | 188–189 |
| 200 | " | H | " | " | CH₂C₆H₅ | " | 0 | 102–103 |
| 201 | " | COC₆H₅ | " | NO₂ | CH₃ | " | " | 209–210 |
| 202 | " | H | " | CF₃ | i-C₃H₇ | " | " | 55–56 |
| 203 | " | " | " | " | " | " | 1 | 134–135 |
| 204 | " | Cl | " | " | " | " | 0 | 94–95 |
| 205 | " | " | " | " | " | " | 1 | 148–149 |
| 206 | " | " | " | " | i-C₄H₉ | " | 0 | 78–79 |
| 207 | " | " | " | " | " | " | 1 | 129–130 |
| 208 | " | H | F | CH₃ | CH₃ | " | 0 | 116–119 |
| 209 | " | " | " | " | " | " | 1 | 182–184 |
| 210 | " | " | H | CF₃ | CH₂SC₆H₅ | " | 0 | 149–150 |
| 211 | Cl | H | H | CH₃ | ▷ | CH₃ | " | 100–101 |
| 212 | " | " | " | " | " | " | 1 | 208–209 |
| 213 | H | " | Cl | H | i-C₃H₇ | " | 0 | 218–220 |
| 214 | " | " | " | " | " | " | 1 | 211–213 |

TABLE 2

4-alkoxy or 4-aryloxy-2-quinolinone(Ic)

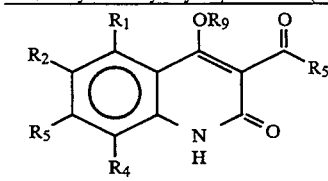

| Comp. No. | R₁ | R₂ | R₃ | R₄ | R₅ | R₉ | m.p. (°C.) |
|---|---|---|---|---|---|---|---|
| 215 | H | Cl | H | CF₃ | CH₃ | C₂H₅ | 79–80 |
| 216 | " | H | " | " | " | n-C₃H₇ | — |
| 217 | " | " | " | " | " | cyclohexyl | 57–58 |
| 218 | " | " | " | " | " | i-C₃H₇ | 103–104 |

TABLE 2-continued 4-alkoxy or 4-aryloxy-2-quinolinone(Ic)

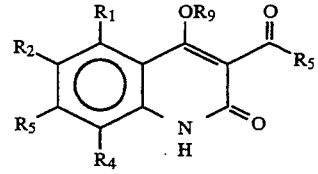

| Comp. No. | R₁ | R₂ | R₃ | R₄ | R₅ | R₉ | m.p. (°C.) |
|---|---|---|---|---|---|---|---|
| 219 | " | " | " | " | " | n-C₄H₉ | 31–32 |
| 220 | " | " | Cl | Cl | " | 4-F-C₆H₄ | 192–193 |
| 221 | Cl | " | H | " | " | " | 165–166 |
| 222 | H | Cl | " | CF₃ | " | " | 157–158 |

TABLE 3
4-amino-2-quinolinone(Id)
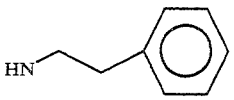
| Comp. No. | $R_1$ | $R_2$ | $R_3$ | $R_4$ | $CH_3$ | NAB | m.p.(°C.) |
|---|---|---|---|---|---|---|---|
| 223 | H | Cl | H | $CF_3$ | $CH_3$ |  | 149–151 |
| 224 | " | " | " | " | " | 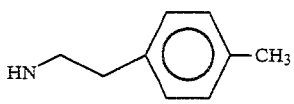 | 177–178 |
| 225 | " | " | " | " | " | 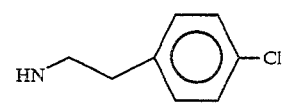 | 135–136 |
| 226 | " | " | " | " | " | 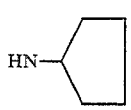 | 218–220 |
| 227 | " | " | " | " | " | 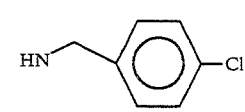 | 166–168 |
| 228 | " | " | " | " | " |  | 217–218 |
| 229 | " | H | " | Cl | $C_2H_5$ | 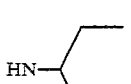 | 164–166 |
| 230 | " | " | " | $CH_3$ | $CH_3$ | " | 158–161 |
| 231 | " | Cl | " | $CF_3$ | " | 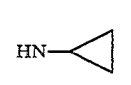 | 113–115 |
| 232 | " | " | " | " | " |  | 195–197 |
| 233 | " | " | " | " | " | 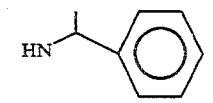 | 139–144 |
| 234 | " | " | " | " | " | 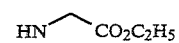 | 173–174 |
| 235 | " | " | " | " | " | HN—$CO_2C_2H_5$ | 153–155 |

TABLE 3-continued 4-amino-2-quinolinone(Id)

| Comp. No. | R₁ | R₂ | R₃ | R₄ | CH₃ | NAB | m.p.(°C.) |
|---|---|---|---|---|---|---|---|
| 236 | " | " | " | " | " | HN-propyl | 133–134 |
| 237 | " | " | " | " | " | morpholine (N-linked) | 149–151 |
| 238 | " | " | " | " | " | HN-isobutyl | 113–115 |
| 239 | " | " | " | " | " | HN-isopentyl | 145–147 |
| 240 | " | " | " | " | " | HN-CH₂CH₂-(3,4-dimethoxyphenyl) | 137–140 |
| 241 | " | " | " | " | " | HN-CH(CH₃)CH₂OCH₃ | 188–190 |
| 242 | " | " | " | " | " | HN-N(2,6-dimethylpiperidinyl) | 113–114 |
| 243 | H | Cl | H | CF₃ | CH₃ | HN-(2-methylcyclohexyl) | 131–135 |
| 244 | " | " | " | " | " | HN-heptyl | 71–74 |
| 245 | " | " | " | " | " | HN-CH(CH₃)CH(CH₃)₂ | 111–113 |
| 246 | " | " | " | " | " | 1,2,3,4-tetrahydroisoquinolin-2-yl | 168–170 |
| 247 | " | " | " | " | " | HN-CH₂CH₂-(4-fluorophenyl) | 189–191 |
| 248 | " | H | " | F | " | HN-propyl | — |
| 249 | " | " | " | " | " | HN-CH(CH₃)CH₂OCH₃ | 142–145 |

TABLE 3-continued
4-amino-2-quinolinone(Id)
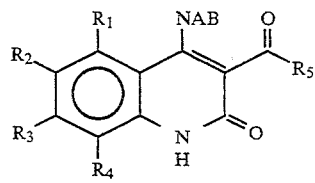
| Comp. No. | R₁ | R₂ | R₃ | R₄ | CH₃ | NAB | m.p.(°C.) |
|---|---|---|---|---|---|---|---|
| 250 | " | Cl | " | CF₃ | " | HN-hexyl | 66–68 |
| 251 | " | " | " | " | " | HN-ethyl | 171–173 |
| 252 | " | " | " | " | " | HN-piperidine-N-CO₂C₂H₅ | 157–159 |
| 253 | " | " | " | " | " | HN-CH(Ph)CH₂OH | 163–167 |
| 254 | " | H | " | F | " | NHCH₃ | 146–150 |
| 255 | " | " | " | " | " | NHC₂H₅ | — |
| 256 | " | " | " | " | " | HN-(2-methylcyclohexyl) | 151–153 |
| 257 | " | Cl | " | CF₃ | " | HN-CH₂CH(CH₃)Ph | 128–131 |
| 258 | " | " | " | " | " | HN-CH₂C(Ph)₂H | 150–152 |
| 259 | " | " | " | " | " | NHCH₃ | 214–216 |
| 260 | " | H | " | " | " | HN-CH(CH₃)Ph | 196–198 |
| 261 | " | " | " | " | " | HN-CH₂CH₂CH(CH₃)₂ | 137–140 |
| 262 | " | " | " | " | " | HN-ethyl | 160–161 |
| 263 | H | H | H | CF₃ | CH₃ | HN-propyl | 148–153 |

TABLE 3-continued

4-amino-2-quinolinone(Id)

[Structure: quinolinone with R1, R2, R3, R4 substituents on benzene ring, NAB at position 4, C(O)R5 at position 3, CH3 group, and N-H]

| Comp. No. | R₁ | R₂ | R₃ | R₄ | CH₃ | NAB | m.p.(°C.) |
|---|---|---|---|---|---|---|---|
| 264 | " | " | " | " | " | 1,2,3,4-tetrahydroisoquinolin-2-yl | 124–126 |
| 265 | " | " | " | " | " | HN–CH(CH₃)CH₂OCH₃ | 167–169 |
| 266 | " | " | " | " | " | NHCH₃ | |
| 267 | " | " | " | " | " | HN–CH₂CH₂CH(CH₃)₂ | 141–143 |
| 268 | " | " | " | " | " | HN–CH(CH₂CH₃)₂ | 131–133 |
| 269 | " | " | " | " | " | HN–(CH₂)₉CH₃ | 128–130 |
| 270 | " | " | " | " | " | HN–CH₂CH₂–(pyrrolidin-1-yl) | 178–180 |
| 271 | " | " | " | " | " | HN–CH₂CH₂–(3,4-dimethoxyphenyl) | 159–163 |
| 272 | " | Cl | " | " | " | HN–(CH₂)₄CH₃ | 92–93 |
| 273 | " | " | " | " | " | HN–CH(CH₂CH₃)(CH₂)₄CH₃ | 89–92 |
| 274 | " | " | " | " | " | HN–CH₂CH₂–(4-bromophenyl) | 179–181 |
| 275 | " | " | " | " | " | HN–(1,2,3,4-tetrahydronaphth-1-yl) | 199–202 |
| 276 | " | " | " | " | " | HN–(CH₂)₈CH₃ | 71–74 |
| 277 | " | " | " | " | " | HN–CH(Ph)CH₂Ph | 173–174 |

TABLE 3-continued
4-amino-2-quinolinone(Id)
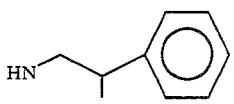
| Comp. No. | $R_1$ | $R_2$ | $R_3$ | $R_4$ | $CH_3$ | NAB | m.p.(°C.) |
|---|---|---|---|---|---|---|---|
| 278 | $NO_2$ | H | " | F | " | 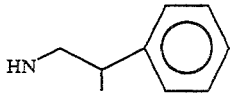 | 230–231 |
| 279 | H | " | " | CN | " | 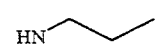 | 159–162 |
| 280 | " | " | " | $CF_3$ | " | 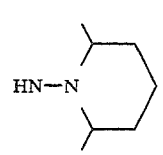 | 132–135 |
| 281 | " | " | " | " | " | 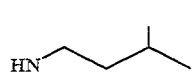 | — |
| 282 | " | F | Cl | H | " | 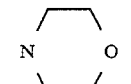 | 254–256 |
| 283 | H | F | Cl | H | $CH_3$ | 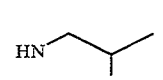 | 190–192 |
| 284 | " | Cl | H | Cl | " | 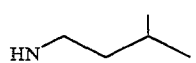 | 166–167 |
| 285 | " | " | " | " | " | 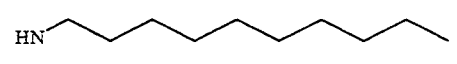 | 168–169 |
| 286 | " | " | " | " | " | 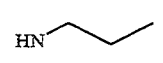 | 143–144 |
| 267 | " | " | " | " | " | 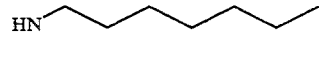 | 167–168 |
| 288 | " | " | " | " | " | 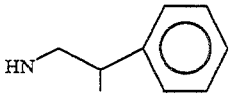 | 119–120 |
| 289 | " | " | " | " | " |  | 102–103 |
| 290 | $NO_2$ | H | " | F | " | 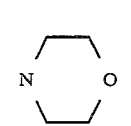 | 231–233 |
| 291 | H | " | " | $CF_3$ | " | 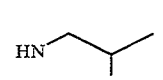 | 80–86 |

TABLE 3-continued 4-amino-2-quinolinone(Id)

| Comp. No. | R₁ | R₂ | R₃ | R₄ | CH₃ | NAB | m.p.(°C.) |
|---|---|---|---|---|---|---|---|
| 292 | " | Cl | " | Cl | " | HN-CH(Ph)-CH₂Ph | 202–203 |
| 293 | " | " | " | " | " | HN-CH(CH₃)-CH(CH₃)₂ | 100–101 |
| 294 | " | " | " | " | " | HN-(CH₂)₆CH₃ | 130–131 |
| 295 | " | " | " | " | " | HN-(CH₂)₉CH₃ | 107–108 |
| 296 | " | " | " | " | " | HN-(CH₂)₄CH₃ | 146–148 |
| 297 | " | " | " | " | " | HN-CH₂CH₂-C₆H₄-CH₃ (p) | 158–159 |
| 298 | " | " | " | " | " | HN-CH₂CH₂-N(pyrrolidinyl) | 186–188 |
| 299 | " | F | Cl | H | " | HN-CH₂CH₃ | 194–196 |
| 300 | CF₃ | H | H | Cl | " | HN-CH₂CH₂-C₆H₄-F (p) | 174–175 |
| 301 | " | " | " | " | " | HN-CH₂CH₃ | 205–207 |
| 302 | " | " | " | " | " | HN-CH₂CH₂CH(CH₃)₂ | 208–209 |
| 303 | " | " | " | " | " | morpholino | 142–143 |
| 304 | H | " | " | CF₃ | " | HN-CH(cyclopropyl)-C₆H₅ | 178–180 |
| 305 | " | " | " | " | " | HN-CH₂-CH(CH₃)-C₆H₅ | 111–113 |
| 306 | NO₂ | H | H | Cl | CH₃ | HN-CH₂CH₂CH(CH₃)₂ | 224–229 |

TABLE 3-continued 4-amino-2-quinolinone(Id)

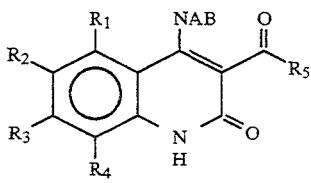

| Comp. No. | R₁ | R₂ | R₃ | R₄ | CH₃ | NAB | m.p.(°C.) |
|---|---|---|---|---|---|---|---|
| 307 | " | " | " | " | " | HN–CH₂CH₂–C₆H₄–F (4-F) | 191–200 |
| 308 | " | " | " | " | " | HN–CH₂–C₆H₄–Cl (4-Cl) | 217–220 |
| 309 | " | " | " | " | " | HN–CH₂–CH(CH₃)–C₆H₅ | 249–250 |
| 310 | H | Cl | " | " | " | HN–CH(CH₃)–CH₂OCH₃ | 193–194 |
| 311 | " | " | " | " | " | HN–(2-methylcyclohexyl) | 162–163 |
| 312 | " | " | " | " | " | HN–CH(CH₃)–C₆H₅ | 175–176 |
| 313 | " | " | " | " | " | HN–CH(CH₃)–CO₂C₂H₅ | 142–143 |
| 314 | " | F | Cl | H | " | HN–CH₂CH₂–C₆H₄–CH₃ | 259–262 |
| 315 | " | H | H | CF₃ | " | HN–CH₂–C₆H₄–Cl | 190–193 |
| 316 | NO₂ | " | " | Cl | " | HN–CH(Ph)–CH₂Ph | 215–217 |
| 317 | " | " | " | " | " | HN–CH(CH₃)–(CH₂)₄CH₃ | 150–153 |
| 318 | " | " | " | " | " | HN–CH₂–CH(CH₃)₂ | 216–218 |
| 319 | " | " | " | " | " | HN–CH₂–CH(OCH₃)₂ | 201–203 |

TABLE 3-continued 4-amino-2-quinolinone(Id)

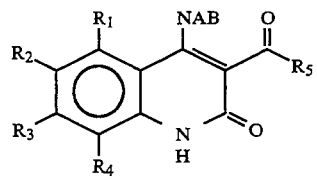

| Comp. No. | R₁ | R₂ | R₃ | R₄ | CH₃ | NAB | m.p.(°C.) |
|---|---|---|---|---|---|---|---|
| 320 | H | F | Cl | H | " | HN—(CH₂)₉CH₃ | 193–195 |
| 321 | NO₂ | H | H | Cl | " | HN—CH₂CH₂—N(pyrrolidinyl) | 217–219 |
| 322 | " | " | " | " | " | HN—CH(CH₃)—Ph | 200–203 |
| 323 | " | " | " | " | " | HN—CH(CH₃)—CH(CH₃)₂ | 221–223 |
| 324 | " | " | " | " | " | HN—(2-methylcyclohexyl) | 228–230 |
| 325 | " | " | " | " | " | HN—(1-CO₂C₂H₅-piperidin-4-yl) | 232–234 |
| 326 | " | " | " | " | " | HN—CH₂CH₂—C₆H₄—NH₂ | 214–215 |
| 327 | H | F | Cl | H | " | HN—CH₂CH(CH₃)₂ | 257–260 |
| 328 | H | F | Cl | H | CH₃ | HN—CH₂—CH(CH₃)—Ph | >260 |
| 329 | " | H | H | CF₃ | " | HN—N(2,2,6,6-tetramethylpiperidinyl) | 113–116 |
| 330 | " | " | " | " | " | HN—CH₂CH₂CH₂—Ph | 105–107 |
| 331 | " | Cl | " | CH₃ | " | HN—CH₂—(2-CF₃-C₆H₄) | 231–233 |

TABLE 3-continued 4-amino-2-quinolinone(Id)

| Comp. No. | R₁ | R₂ | R₃ | R₄ | CH₃ | NAB | m.p.(°C.) |
|---|---|---|---|---|---|---|---|
| 332 | " | " | " | " | " | HN-(CH₂)₆-CH₃ (n-heptyl) | 121–124 |
| 333 | " | " | " | " | " | HN-CH(CH₃)-CH(CH₃)₂ | 148–150 |
| 334 | " | " | " | " | " | HN-(CH₂)₇-CH₃ (n-octyl) | 122–126 |
| 335 | " | " | " | " | " | HN-(2-methylcyclohexyl) | 118–122 |
| 336 | " | " | " | " | " | HN-CH₂-CH₂-CH(CH₃)₂ (isopentyl) | 158–160 |
| 337 | " | " | " | " | " | HN-(CH₂)₉-CH₃ (n-decyl) | 111–112 |
| 338 | " | " | " | " | " | HN-CH₂-CH(OCH₃)₂ | 205–209 |
| 339 | " | " | " | " | " | HN-CH₂-CH₂-(3,4-dimethoxyphenyl) | 190–192 |
| 340 | " | " | " | " | " | HN-CH₂-CH₂-(pyrrolidin-1-yl) | 195–197 |
| 341 | " | " | " | " | " | HN-CH(CH₃)-phenyl | 181–183 |
| 342 | " | H | " | CF₃ | " | HN-CH₂-CH(CH₃)₂ (isobutyl) | 135–137 |
| 343 | " | " | " | " | " | HN-CH₂-CH₂-(2-methoxyphenyl) | 135–137 |
| 344 | " | " | " | " | " | HN-CH₂-CH₂-(4-methylphenyl) | 169–171 |

TABLE 3-continued
4-amino-2-quinolinone(Id)
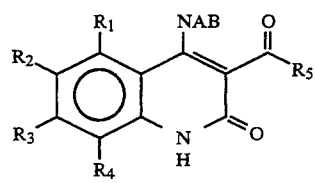
| Comp. No. | R₁ | R₂ | R₃ | R₄ | CH₃ | NAB | m.p.(°C.) |
|---|---|---|---|---|---|---|---|
| 345 | " | " | " | " | " | HN-CH(Ph)-CH₂Ph | 164–166 |
| 346 | " | " | " | " | " | HN-CH₂-(2,4-diCl-C₆H₃) | 180–183 |
| 347 | " | Cl | " | Cl | " | morpholino | 118–120 |
| 348 | H | Cl | H | Cl | CH₃ | HN-CH(Et)(Et) | 120–121 |
| 349 | " | " | " | " | " | HN-CH(CH₃)(n-C₆H₁₃) | 94–95 |
| 350 | " | " | " | " | " | HN-CH(Et)(n-C₄H₉) | — |
| 351 | " | F | Cl | H | " | HN-CH₂CH₂-pyrrolidinyl | 234–236 |
| 352 | " | NO₂ | H | " | " | HN-CH₂-CH(CH₃)₂ | >260 |
| 353 | " | " | " | " | " | HN-CH₂CH₂-CH(CH₃)₂ | 254–256 |
| 354 | " | H | " | CF₃ | " | HN-cyclopentyl | 205–208 |
| 355 | " | " | " | " | " | HN-CH₂-(4-CF₃-C₆H₄) | 181–185 |
| 356 | " | " | " | " | " | HN-CH₂-(2,4-diF-C₆H₃) | 159–164 |
| 357 | " | t-C₄H₉ | " | H | " | HN-C₂H₅ | 217–219 |

TABLE 3-continued
4-amino-2-quinolinone(Id)
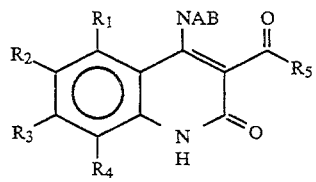
| Comp. No. | R₁ | R₂ | R₃ | R₄ | CH₃ | NAB | m.p.(°C.) |
|---|---|---|---|---|---|---|---|
| 358 | " | " | " | " | " | HN–CH₂–phenyl | 182–184 |
| 359 | " | " | " | " | " | HN–n-pentyl | 219–220 |
| 360 | " | " | " | " | " | HN–CH₂–(3-CF₃-phenyl) | 243–245 |
| 361 | " | " | " | " | " | HN–(CH₂)₃–phenyl | 185–186 |
| 362 | " | " | " | " | " | HN–CH₂–(1-ethylpyrrolidin-3-yl) | 141–143 |
| 363 | " | H | " | CF₃ | " | HN–CH₂–(pyridin-2-yl) | 188–190 |
| 364 | " | " | " | " | " | HN–CH(OCH₃)₂ | 142–143 |
| 365 | " | Cl | " | Cl | " | HN–CH(iPr)–CO₂C₂H₅ | 118–120 |
| 366 | " | t-C₄H₉ | " | H | " | NHC₂H₅ | 266–267 |
| 367 | " | " | " | " | " | HN–CH₂–(2-CF₃-phenyl) | 233–235 |
| 368 | " | Cl | " | CH₃ | " | HN–CH(CH₃)–CH(CH₃)₂ | 112–116 |
| 369 | H | Cl | H | CH₃ | CH₃ | HN–(CH₂)₃–phenyl | 168–170 |

TABLE 3-continued 4-amino-2-quinolinone(Id)

| Comp. No. | R₁ | R₂ | R₃ | R₄ | CH₃ | NAB | m.p.(°C.) |
|---|---|---|---|---|---|---|---|
| 370 | " | " | " | " | " | HN-CH₂CH₂-(2-CH₃O-C₆H₄) | 164–167 |
| 371 | " | " | " | " | " | HN-(1,2,3,4-tetrahydronaphthalen-1-yl) | 201–203 |
| 372 | " | " | " | " | " | HN-CH₂-(4-CF₃-C₆H₄) | 186–191 |
| 373 | " | " | " | " | " | HN-CH₂CH₂-(4-Cl-C₆H₄) | 208–209 |
| 374 | " | " | " | " | " | HN-n-C₅H₁₁ | 154–155 |
| 375 | " | " | " | " | " | HN-CH₂-(2,6-F₂-C₆H₃) | 178–182 |
| 376 | " | t-C₄H₉ | " | H | " | HN-CH₂CH₂CH₂-Cl | 175–176 |
| 377 | " | " | " | " | " | HN-cyclobutyl | 253–254 |
| 378 | " | " | " | " | " | HN-CH₂-cyclopropyl | 231–233 |
| 379 | " | Cl | " | CH₃ | " | HN-CH₂-(1-C₂H₅-pyrrolidin-2-yl) | 170–172 |
| 380 | " | " | " | " | " | HN-CH₂-CH(Ph)₂ | 193–196 |
| 381 | " | " | " | " | " | HN-CH₂-cyclopropyl | 193–195 |

TABLE 3-continued 4-amino-2-quinolinone(Id)

| Comp. No. | $R_1$ | $R_2$ | $R_3$ | $R_4$ | $CH_3$ | NAB | m.p.(°C.) |
|---|---|---|---|---|---|---|---|
| 382 | " | " | " | " | " | HN-CH(CH₂OH)-C₆H₅ | 239-241 |
| 383 | " | " | " | " | " | HN-CH₂-(2-pyridyl) | 255-257 |
| 384 | " | " | " | " | " | HN-(2-phenylcyclopropyl) | 219-220 |
| 385 | " | " | " | " | " | NHC₂H₅ | 202-203 |
| 386 | " | H | " | $C_2H_5$ | " | HN-CH(CH₃)-C₆H₅ | 168-169 |
| 387 | " | " | " | " | " | HN-CH₂-(2-CF₃-C₆H₄) | 186-187 |
| 388 | " | " | " | " | " | HN-CH₂-CH₂-CH(CH₃)₂ | 169-171 |
| 389 | H | H | H | $C_2H_5$ | $CH_3$ | HN-CH₂-CH₂-(3,4-diOCH₃-C₆H₃) | 188-190 |
| 390 | " | " | " | " | " | HN-(n-C₁₀H₂₁) | 80-82 |
| 391 | " | " | " | " | " | HN-(n-C₈H₁₇) | 114-115 |
| 392 | " | " | " | " | " | HN-CH₂-(2,4-diCl-C₆H₃) | 163-164 |
| 393 | " | " | " | " | " | HN-CH₂-(4-Cl-C₆H₄) | 143-145 |
| 394 | " | " | " | " | " | HN-CH₂-cyclopropyl | 137-139 |

TABLE 3-continued 4-amino-2-quinolinone(Id)

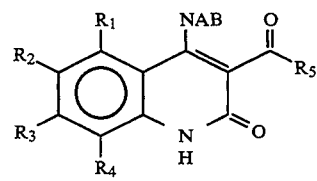

| Comp. No. | R₁ | R₂ | R₃ | R₄ | CH₃ | NAB | m.p.(°C.) |
|---|---|---|---|---|---|---|---|
| 395 | " | " | " | " | " | HN–CH₂CH₂–pyrrolidinyl | 181–183 |
| 396 | " | " | " | " | " | HN–CH₂–CH(CH₃)–(4-methylphenyl) | 108–109 |
| 397 | " | " | " | " | " | HN–CH₂–CH(CH₃)–phenyl | 99–100 |
| 398 | " | " | " | " | " | HN–(2-methylcyclohexyl) | 148–150 |
| 399 | " | " | " | " | " | HN–CH₂CH₂–(4-chlorophenyl) | 150–153 |
| 400 | " | " | " | " | " | HN–cyclopentyl | 114–116 |
| 401 | " | " | " | " | " | HN–CH₂–(2,6-difluorophenyl) | 180–182 |
| 402 | " | " | " | " | " | HN–CH₂CH₂CH₂–phenyl | 139–140 |
| 403 | " | " | " | " | " | HN–CH₂CH₂–(4-fluorophenyl) | 148–150 |
| 404 | " | Cl | " | CF₃ | " | HN–CH(CH₃)CH₂CH₃ | 127–128 |
| 405 | " | " | " | " | " | HN–CH₂–CH(OCH₃)₂ | 192–194 |

TABLE 3-continued
4-amino-2-quinolinone(Id)
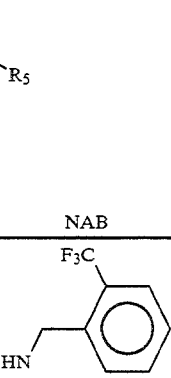
| Comp. No. | R₁ | R₂ | R₃ | R₄ | CH₃ | NAB | m.p.(°C.) |
|---|---|---|---|---|---|---|---|
| 406 | " | " | " | " | " | 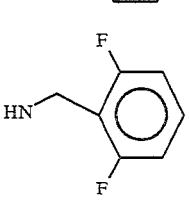 | 228-231 |
| 407 | " | " | " | " | " | 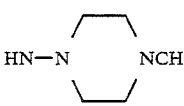 | 171-172 |
| 408 | " | " | " | " | " | 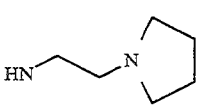 | 203-205 |
| 409 | " | " | " | " | " | 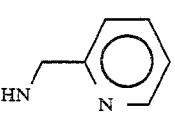 | 244-246 |
| 410 | H | Cl | H | CF₃ | CH₃ | 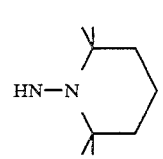 | 226-228 |
| 411 | " | " | " | " | " | 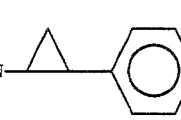 | 332-335 |
| 412 | " | " | " | " | " | 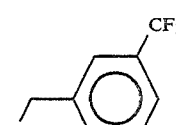 | 173-175 |
| 413 | " | " | " | CH₃ | " | 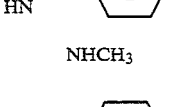 | 216-220 |
| 414 | " | " | " | " | " | NHCH₃ | 250-252 |
| 415 | " | " | " | " | " |  | 221-222 |
| 416 | " | " | " | " | " | 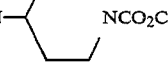 | 209-211 |

TABLE 3-continued 4-amino-2-quinolinone(Id)

$$\text{[Structure: quinolin-2(1H)-one with } R_1, R_2, R_3, R_4 \text{ on benzene ring, NAB at 4-position, and C(=O)R}_5 \text{ at 3-position]}$$

| Comp. No. | R₁ | R₂ | R₃ | R₄ | CH₃ | NAB | m.p.(°C.) |
|---|---|---|---|---|---|---|---|
| 417 | " | " | " | " | " | HN–CH₂–C₆H₄–NO₂ (4-) | 210–212 |
| 418 | " | " | " | " | " | HN–N(piperazine)–NCH₃ | 141–160 |
| 419 | " | " | " | " | " | HN–CH₂CH₂–C₆H₄–SO₂NH₂ (4-) | 305–308 |
| 420 | " | " | " | " | " | HN–CH₂CH₂–C₆H₄–F (4-) | 195–197 |
| 421 | " | " | " | " | " | HN–CH₂–CH(CH₃)–C₆H₅ | 141–144 |
| 422 | " | " | " | " | " | HN–CH(CH₃)–CO₂C₂H₅ | 155–156 |
| 423 | " | " | " | " | " | HN–cyclopentyl | 194–195 |
| 424 | " | " | " | " | " | N(piperidinyl)–piperidine | 165–167 |
| 425 | " | " | " | " | " | HN–CH₂CH₂–C₆H₄–NO₂ (4-) | 196–198 |
| 426 | " | t-C₄H₉ | " | " | " | HN–CH₂–C₆H₃(2,6-F₂) | 231–232 |
| 427 | " | " | " | " | " | HN–CH₂–C₆H₃(2,4-F₂) | 235–236 |

TABLE 3-continued 4-amino-2-quinolinone(Id)

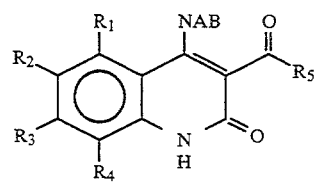

| Comp. No. | R$_1$ | R$_2$ | R$_3$ | R$_4$ | CH$_3$ | NAB | m.p.(°C.) |
|---|---|---|---|---|---|---|---|
| 428 | " | " | " | " | " | HN–CH$_2$–CH(OCH$_3$)$_2$ | 161–163 |
| 429 | " | " | " | " | " | HN–CH$_2$CH$_2$–(3,4-dimethoxyphenyl) | 187–189 |
| 430 | H | t-C$_4$H$_9$ | H | H | CH$_3$ | HN–CH(CH$_3$)CH$_2$OCH$_3$ | 172–173 |
| 431 | " | " | " | " | " | HN–CH(CH$_3$)CH$_2$CH$_3$ | 208–210 |
| 432 | " | " | " | " | " | HN–CH(C$_2$H$_5$)$_2$ | 217–218 |
| 433 | " | " | " | " | " | HN–CH$_2$–(2,4-dichlorophenyl) | 253–255 |
| 434 | " | " | " | " | " | HN–N(2,6-dimethylpiperidinyl) | 236–238 |
| 435 | " | Cl | " | CF$_3$ | " | HN–CH$_2$CH$_2$CH$_2$Cl | 122–124 |
| 436 | " | " | " | " | " | HN–CH$_2$–(2,4-dichlorophenyl) | 167–169 |
| 437 | " | " | " | " | " | HN–CH$_2$–(2,4-difluorophenyl) | 202–204 |
| 438 | " | " | " | " | " | HN–CH$_2$–(3-trifluoromethylphenyl) | 204–206 |

| | | | | | | |
|---|---|---|---|---|---|---|
| 439 | " | " | " | " | " | 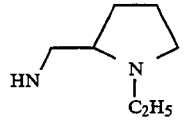 | 184–186 |
| 440 | " | " | " | " | " | 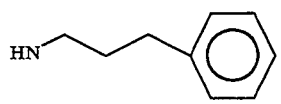 | 126–129 |
| 441 | " | " | " | " | " | 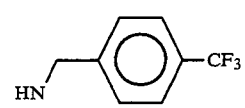 | 173–174 |
| 442 | CF$_3$ | H | " | Cl | " | 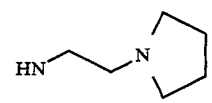 | 206–208 |
| 443 | " | " | " | " | " | 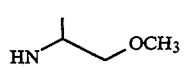 | 168–170 |
| 444 | " | " | " | " | " | 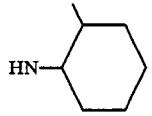 | 165–167 |
| 445 | " | " | " | " | " | 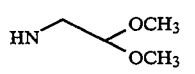 | 184–187 |
| 446 | " | " | " | " | " | 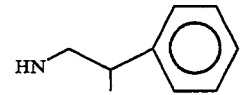 | 178–179 |
| 447 | " | " | " | " | " | 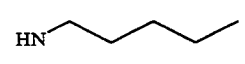 | 173–175 |
| 448 | H | BR | CF$_3$ | H | " | 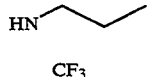 | 231–233 |
| 449 | " | " | " | " | " | 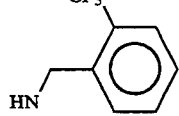 | 213–215 |
| 450 | H | BR | CF$_3$ | H | CH$_3$ | 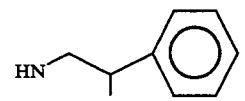 | 258–259 |
| 451 | " | " | " | " | " | 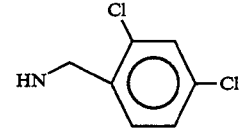 | 261–263 |
| 452 | " | " | " | " | " | 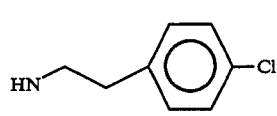 | 275–278 |

-continued

| No. | | | | | | Amine | mp |
|---|---|---|---|---|---|---|---|
| 453 | " | " | " | " | " | 4-chlorobenzylamino (HN-CH2-C6H4-Cl) | 232-234 |
| 454 | CF₃ | H | H | Cl | " | 2-methoxyphenethylamino | 189-190 |
| 455 | " | " | " | " | " | 2,4-dichlorobenzylamino | 235-238 |
| 456 | " | " | " | " | " | 4-(trifluoromethyl)benzylamino | 225-226 |
| 457 | " | " | " | " | " | (1-ethylpyrrolidin-2-yl)methylamino | 186-188 |
| 458 | " | " | " | " | " | cyclopentylamino | 174-176 |
| 459 | " | " | " | " | " | cyclopropylmethylamino | 218-219 |
| 460 | " | " | " | " | " | 3-(trifluoromethyl)benzylamino | 231-235 |
| 461 | " | " | " | " | " | 4-nitrophenethylamino | 208-210 |
| 462 | H | Cl | CF₃ | H | " | (pyridin-2-yl)methylamino | 239-240 |
| 463 | " | " | " | " | " | 4-methylphenethylamino | 223-226 |
| 464 | " | " | " | " | " | (R)-α-methylphenethylamino | 249-250 |
| 465 | " | " | " | " | " | 2,4-difluorobenzylamino | 259-260 |

-continued
| | | | | | | |
|---|---|---|---|---|---|---|
| 466 | " | " | " | " | " | 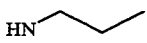 | 217-222 |
| 467 | " | " | " | " | " | 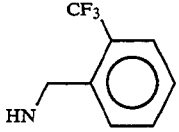 | 232-234 |
| 468 | " | " | " | " | " | 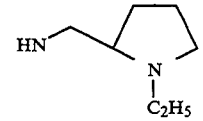 | 192-194 |
| 469 | " | H | " | " | " | 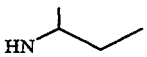 | 233-235 |
| 470 | H | H | CF₃ | H | CH₃ | 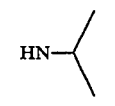 | 238-240 |
| 471 | " | " | " | " | " | 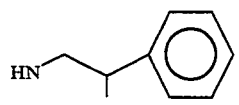 | 266-268 |
| 472 | " | " | " | " | " | 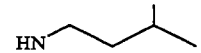 | 234-236 |
| 473 | " | " | " | " | " | 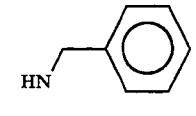 | 251-252 |
| 474 | " | " | " | " | " |  | 238-239 |
| 475 | " | " | Cl | Cl | " |  | 110-111 |
| 476 | " | " | " | " | " | 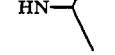 | 162-164 |
| 477 | " | " | " | " | " | 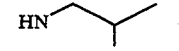 | 190-198 |
| 478 | " | " | " | " | " | 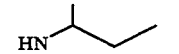 | 133-135 |
| 479 | " | " | " | " | " |  | 112-114 |
| 480 | " | " | " | " | " | 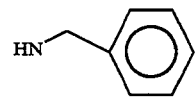 | 201-203 |
| 481 | " | " | " | " | " | 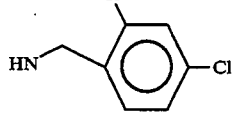 | 173-174 |

| | | | | | | |
|---|---|---|---|---|---|---|
| 482 | " | " | " | " | " | 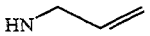 | 175-176 |
| 483 | " | " | " | " | " | 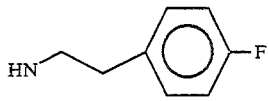 | 172-173 |
| 484 | " | " | " | " | " | 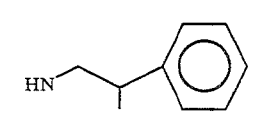 | 150-151 |
| 485 | " | " | " | " | " |  | 153-155 |
| 486 | " | " | " | " | " | 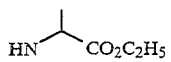 | 85-86 |
| 487 | " | " | " | " | " | 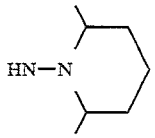 | 197-198 |
| 488 | " | " | " | " | " | NHCH$_3$ | 213-215 |
| 489 | CF$_3$ | " | H | " | " |  | 177-178 |
| 490 | " | " | " | " | " | 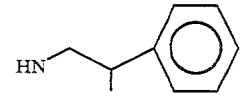 | 211-213 |
| 491 | " | " | " | " | " |  | 133-135 |
| 492 | CF$_3$ | H | H | Cl | CH$_3$ | 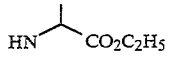 | 209-212 |
| 493 | " | " | " | " | " | 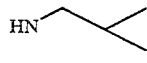 | 222-224 |
| 494 | " | " | " | " | " | 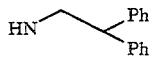 | 160-161 |
| 495 | Cl | " | " | " | " | 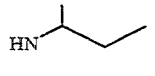 | 179-180 |
| 496 | " | " | " | " | " | 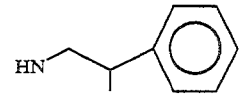 | 205 |
| 497 | " | " | " | " | " | 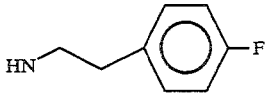 | 216-217 |

-continued

| # | | | | | | Amine | mp |
|---|---|---|---|---|---|---|---|
| 498 | " | " | " | " | " | HN-CH2-C6H5 (benzylamine) | 232–234 |
| 499 | " | " | " | " | " | HN-CH2CH(CH3)2 (isobutyl, via CH2) — isoamyl (HN-CH2CH2CH(CH3)2) | 175–177 |
| 500 | " | " | " | " | " | HN-CH2-CH=CH2 (allyl) | 164–165 |
| 501 | " | " | " | " | " | HN-CH(CH3)2-... isobutyl HN-CH2CH(CH3)2 | 184–185 |
| 502 | " | " | " | " | " | HN-CH(CH3)CH2CH3 (sec-butyl) | 176–178 |
| 503 | " | " | " | " | " | HN-CH2CH2CH3 (n-propyl) | 190–192 |
| 504 | " | " | " | " | " | HN-CH(CH3)2 (isopropyl) | 235–237 |
| 505 | H | Cl | CF$_3$ | H | " | HN-CH2-C6H4-4-NO2 | 239–242 |
| 506 | " | " | " | " | " | HN-CH2CH2-C6H4-4-Cl | 285–286 |
| 507 | " | " | " | " | " | HN-CH2CH2CH2-C6H5 | 167–173 |
| 508 | " | " | " | " | " | HN-(4-piperidinyl)-N-CO2C2H5 | 192–193 |
| 509 | " | " | " | " | " | HN-CH2-cyclopropyl | 211–212 |
| 510 | " | " | " | " | " | HN-CH2-C6H4-4-Cl | 245–247 |
| 511 | " | " | " | " | " | HN-CH2CH2-C6H4-4-NH2 | 235–239 |
| 512 | Cl | H | H | Cl | " | HN-CH(CH3)-CO2C2H5 | 170–173 |
| 513 | " | " | " | " | " | morpholino (N—O ring) | 149–150 |
| 514 | CF$_3$ | " | " | " | " | HN-CH2-CH=CH2 | 223–226 |

| | | | | | | | |
|---|---|---|---|---|---|---|---|
| 515 | H | Cl | H | CH₃ | NHCH₃ | | 266–268 |
| 516 | " | H | " | C₂H₅ | " | | 168–170 |
| 517 | " | OCH₃ | " | H | " | | 248–250 |
| 518 | CF₃ | H | " | Cl | " | | 270–274 |
| 519 | H | H | " | " | "" | | 211–213 |
| 520 | " | Cl | CF₃ | H | " | | 275–277 |
| 521 | " | H | " | " | " |  | 277–279 |
| 522 | " | CF₃ | H | H | " |  | 235–237 |
| 523 | " | " | " | " | " |  | 225–227 |
| 524 | " | " | " | " | " |  | 254–257 |
| 525 | " | Cl | " | CH₃ | " |  | 197–198 |
| 526 | " | " | CF₃ | H | " |  | 111–116 |
| 527 | " | " | " | " | " |  | 276–277 |
| 528 | Cl | H | H | CH₃ | " |  | 164–166 |
| 529 | " | " | " | " | " |  | 215–216 |
| 530 | " | " | " | " | " |  | 184–185 |
| 531 | " | " | " | " | " |  | 207–208 |
| 532 | " | " | " | " | " |  | 182–185 |
| 533 | CH₃ | H | CH₃ | H | " |  | 140–142 |
| 534 | " | " | " | " | " |  | 145–146 |

-continued
| | | | | | | |
|---|---|---|---|---|---|---|
| 535 | " | " | " | " | " |  | 213–214 |
| 536 | " | " | " | " | " | 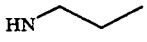 | 220–222 |
| 537 | " | " | " | " | " | 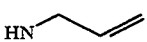 | 117–120 |
| 538 | CH$_3$ | H | CH$_3$ | H | CH$_3$ | 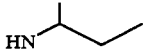 | 203–205 |
| 539 | " | " | " | " | " |  | 182–184 |
| 540 | H | CF$_3$ | H | " | " | 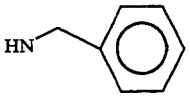 | 205–210 |
| 541 | " | " | " | " | " | 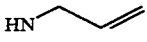 | 137–138 |
| 542 | " | " | " | " | " |  | 124–126 |
| 543 | " | H | " | I-C$_3$H$_7$ | " | 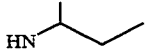 | 126–128 |
| 544 | " | " | " | " | " | 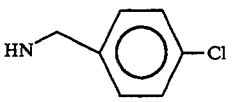 | 154–155 |
| 545 | " | " | " | " | " |  | 107–108 |
| 546 | " | " | " | " | " |  | 114–115 |
| 547 | NO$_2$ | " | " | Cl | " | 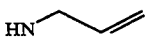 | 202–203 |
| 548 | " | " | " | " | " | 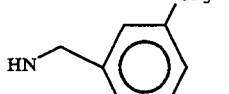 | 258–259 |
| 549 | " | " | " | " | " | 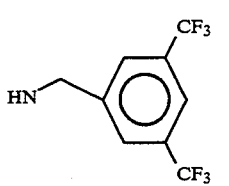 | 251–254 |

-continued

| | | | | | | | |
|---|---|---|---|---|---|---|---|
| 550 | " | " | " | " | " | HN-CH₂-C₆H₄-CF₃ (4-) | 246–248 |
| 551 | " | " | " | " | " | HN-CH₂-C₆H₃-3,4-Cl₂ | 242–245 |
| 552 | " | " | " | " | " | HN-CH₂-C₆H₄-CH₃ (4-) | 206–208 |
| 553 | " | " | " | " | " | HN-CH₂-C₆H₄-CF₃ (2-) | 242–244 |
| 554 | Cl | " | Cl | H | " | HN-CH₂CH₃ | 192–195 |
| 555 | " | " | " | " | " | HN-CH₂-CH(CH₃)₂ | 124–125 |
| 556 | " | " | " | " | " | HN-CH₂CH₂-CH(CH₃)₂ | 128–130 |
| 557 | " | " | H | CH₃ | " | HN-CH(CH₃)₂ | 213–214 |
| 558 | NO₂ | " | " | OCH₃ | " | HN-CH₂CH₃ | 162–165 |
| 559 | " | " | " | " | " | HN-CH₂CH₂-CH(CH₃)₂ | 175–176 |

| | | | | | | | |
|---|---|---|---|---|---|---|---|
| 560 | NO₂ | H | H | OCH₃ | CH₃ | HN-CH₂-CH(CH₃)₂ | 135–138 |
| 561 | " | " | " | " | " | HN-CH₂-C₆H₅ | 178–179 |
| 562 | " | " | " | Cl | " | HN-CH₂-C₆H₃-2,6-F₂ | 219–220 |
| 563 | " | " | " | " | " | HN-CH₂-C₆H₃-2,4-F₂ | 266–269 |

-continued
| | | | | | | |
|---|---|---|---|---|---|---|
| 564 | H | " | " | C₆H₅ | " | 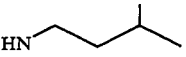 | 142–144 |
| 565 | " | " | " | " | " | 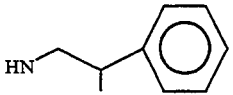 | 134–136 |
| 566 | " | " | " | " | " |  | 168–169 |
| 567 | " | " | " | " | " | 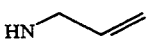 | 198–200 |
| 568 | " | " | " | " | " | 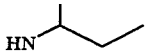 | 156–158 |
| 569 | " | " | " | " | " | NHCH₃ | 196–198 |
| 570 | " | " | " | " | " | 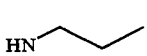 | 178–180 |
| 571 | " | " | " | " | " | 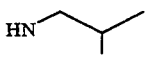 | 182–183 |
| 572 | " | " | " | " | " | 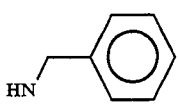 | 200–202 |
| 573 | " | " | " | " | " | 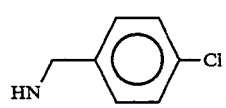 | 127–133 |
| 574 | " | " | " | " | " | 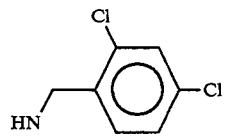 | 193–196 |
| 575 | " | " | " | " | " | 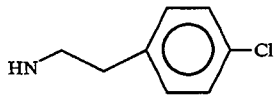 | 170–171 |
| 576 | " | CH₃ | " | CH₃ | " | 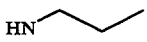 | 185–186 |
| 577 | " | " | " | " | " | 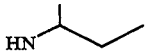 | 108–111 |
| 578 | " | " | " | " | " | 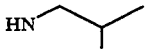 | 128–130 |
| 579 | " | " | " | " | " | 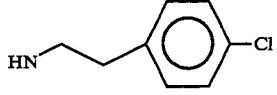 | 182–183 |
| 580 | " | " | " | " | " | 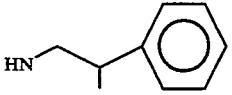 | 85–87 |

| | | | | | | |
|---|---|---|---|---|---|---|
| 581 | " | " | " | " | " | 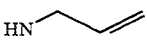 | 163-164 |
| 582 | H | CH$_3$ | H | CH$_3$ | CH$_3$ |  | 150-151 |
| 583 | " | Cl | " | CF$_3$ | " | 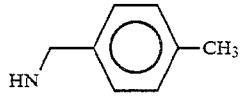 | 166-174 |
| 584 | H | " | " | " | " | 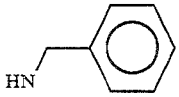 | 164-167 |
| 585 | " | " | " | " | " | 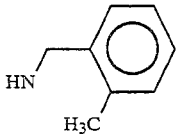 | 157-161 |
| 586 | " | " | " | " | " | 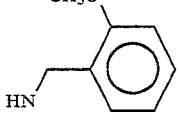 | 158-160 |
| 587 | " | H | " | CH$_2$C$_6$H$_5$ | " |  | 132-134 |
| 588 | " | " | " | " | " | 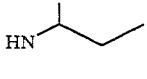 | 97-98 |
| 589 | " | " | " | " | " |  | 98-100 |
| 590 | " | " | " | " | " | 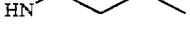 | 146-147 |
| 591 | " | " | " | " | " | 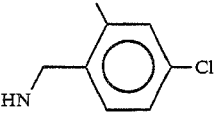 | 131-132 |
| 592 | " | " | " | " | " | 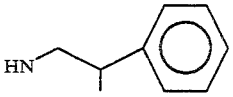 | 138-140 |
| 593 | " | " | " | " | " | 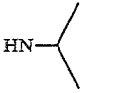 | 119-120 |
| 594 | " | " | " | " | " |  | 153-154 |
| 595 | " | CH$_3$ | " | CH$_3$ | " |  | 222-223 |

-continued

| No. | | | | | | Structure | mp |
|---|---|---|---|---|---|---|---|
| 596 | " | " | " | " | " | 4-Cl-C6H4-CH2-NH- | 237–239 |
| 597 | " | " | " | " | " | 2,4-Cl2-C6H3-CH2-NH- | 223–226 |
| 598 | Cl | H | Cl | H | " | sec-Bu-NH- | 205–207 |
| 599 | NO2 | " | H | OCH3 | " | iPr-NH- | 210–213 |
| 600 | " | " | " | " | " | sec-Bu-NH- | 200–201 |
| 601 | " | " | " | " | " | 2,6-dimethylpiperidin-1-yl-NH- | 133–134 |
| 602 | H | Cl | H | CF3 | CH3 | 4-Cl-C6H4-CH2-NH- | 216–217 |
| 603 | " | H | " | n-C3H7 | " | CH2=CH-CH2-NH- | 168–170 |
| 604 | H | " | " | " | " | 2,4-Cl2-C6H3-CH2-NH- | 174–176 |
| 605 | " | " | " | " | " | 4-Cl-C6H4-CH2CH2-NH- | 127–129 |
| 606 | " | " | " | " | " | C6H5-CH(CH3)-CH2-NH- | 134–136 |
| 607 | " | " | " | " | " | iBu-NH- | 106–108 |
| 608 | " | " | " | " | " | isoamyl-NH- | 104–105 |
| 609 | " | CH3 | " | Cl | " | 4-Cl-C6H4-CH2CH2-NH- | 173–175 |
| 610 | " | " | " | " | " | sec-Bu-NH- | 103–105 |

-continued
| | | | | | | | |
|---|---|---|---|---|---|---|---|
| 611 | " | " | " | " | " |  | 149-150 |
| 612 | " | " | " | " | " | 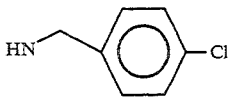 | 248-251 |
| 613 | " | " | " | " | " | 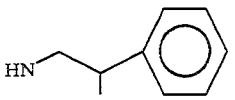 | 147-150 |
| 614 | " | " | " | " | " | 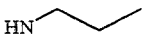 | 161-162 |
| 615 | " | " | " | " | " | 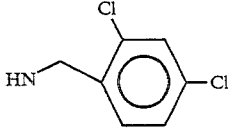 | 231-233 |
| 616 | " | " | " | " | " | 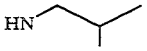 | 128-130 |
| 617 | " | " | " | " | " | 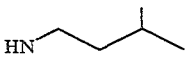 | 135-136 |
| 618 | " | " | " | " | " |  | 171-172 |
| 619 | " | " | " | " | " | 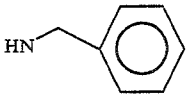 | 236-238 |
| 620 | " | Cl | " | CF$_3$ | " | 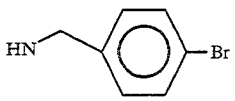 | 214-217 |
| 621 | " | " | " | " | " | 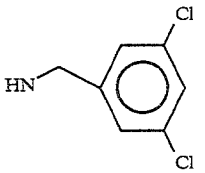 | 228-231 |
| 622 | " | " | " | " | " | 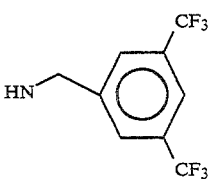 | 201-202 |
| 623 | Cl | H | Cl | H | CH$_3$ |  | 187-188 |
| 624 | H | CH$_3$ | Cl | " | " | 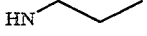 | 252-255 |

-continued

| No. | | | | | Amine | m.p. |
|---|---|---|---|---|---|---|
| 625 | " | " | " | " | HN-CH(CH₃)₂ (isopropylamine) | 228–231 |
| 626 | " | " | " | " | HN-CH₂CH(CH₃)₂ (isobutylamine) | 255–258 |
| 627 | " | " | " | " | HN-CH(CH₃)CH₂CH₃ (sec-butylamine) | 248–251 |
| 628 | " | " | " | " | HN-CH₂CH₂CH(CH₃)₂ (isoamylamine) | 263–265 |
| 629 | " | " | " | " | morpholine | 231–234 |
| 630 | " | " | " | " | HN-CH₂-C₆H₅ (benzylamine) | 257–258 |
| 631 | " | " | " | " | HN-CH(CH₃)CH₂-C₆H₅ | 295–296 |
| 632 | Cl | CH₃ | H | " | HN-CH₂CH=CH₂ (allylamine) | 198–199 |
| 633 | " | " | " | " | HN-CH₂CH₂CH₃ (n-propylamine) | 217–218 |
| 634 | " | " | " | " | HN-CH₂CH(CH₃)₂ | 209–210 |
| 635 | " | " | " | " | HN-CH(CH₃)CH₂CH₃ | 189–190 |
| 636 | " | " | " | " | HN-CH₂CH₂CH(CH₃)₂ | 198–199 |
| 637 | " | " | " | " | morpholine | 219–220 |
| 638 | " | " | " | " | HN-CH₂-C₆H₅ | 201–202 |
| 639 | " | " | " | " | HN-CH(CH₃)CH₂-C₆H₅ | 224–225 |
| 640 | H | Cl | " | F | HN-CH₂CH(CH₃)₂ | 168–170 |
| 641 | " | " | " | " | HN-CH(CH₃)CH₂-C₆H₅ | 148–150 |

-continued
| | | | | | | | |
|---|---|---|---|---|---|---|---|
| 642 | " | " | " | " | " | 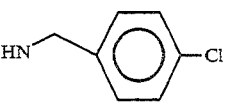 | 244–247 |
| 643 | " | " | " | " | " | 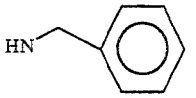 | 138–140 |
| 644 | " | " | " | " | " | 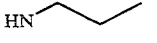 | 235–240 |
| 645 | " | " | " | " | " | 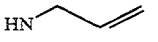 | 169–170 |
| 646 | H | Cl | H | F | CH$_3$ | 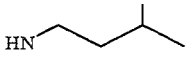 | 198–200 |
| 647 | " | " | " | " | " |  | 151–153 |
| 648 | " | " | " | " | " | 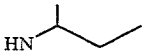 | 150–157 |
| 649 | CH$_3$ | H | " | Cl | " | 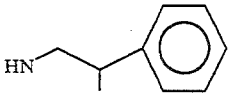 | 113–115 |
| 650 | " | " | " | " | " | 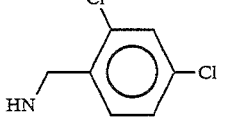 | 131 |
| 651 | " | " | " | " | " | 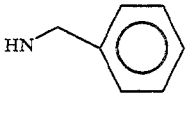 | 178–181 |
| 652 | " | " | " | " | " |  | 187–189 |
| 653 | " | " | " | " | " |  | 105–107 |
| 654 | " | " | " | " | " |  | 133–134 |
| 655 | " | " | " | " | " | 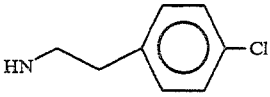 | 174–176 |
| 656 | " | " | " | " | " |  | 162–163 |
| 657 | " | " | " | " | " | 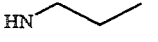 | 121–122 |
| 658 | " | " | " | " | " |  | 137–138 |

-continued

| | | | | | | R | m.p. |
|---|---|---|---|---|---|---|---|
| 659 | " | " | " | " | " | NH-CH(CH₃)₂ (isopropyl) | 142 |
| 660 | " | " | " | " | " | NH-CH₂CH₂CH(CH₃)₂ (isopentyl) | 98–99 |
| 661 | H | F | " | Cl | " | 2-Cl-benzyl-NH | 192–194 |
| 662 | " | " | " | " | " | NH-CH₂CH(CH₃)₂ (isobutyl) | 164–165 |
| 663 | " | " | " | " | " | 4-OCH₃-benzyl-NH | 211–215 |
| 664 | " | " | " | " | " | 2-CF₃-benzyl-NH | 194–197 |
| 665 | " | " | " | " | " | 4-Cl-benzyl-NH | 211–213 |
| 666 | " | " | " | " | " | NH-CH₂CH₂CH₃ (n-propyl) | 123–125 |
| 667 | " | " | " | " | " | benzyl-NH | 210–211 |
| 668 | H | F | H | Cl | CH₃ | morpholino | 140–145 |
| 669 | " | " | " | " | " | NH-CH₂CH(CH₃)-C₆H₅ | 126–127 |
| 670 | " | " | " | " | " | 2,4-diCl-benzyl-NH | 194–197 |
| 671 | " | " | " | " | " | 2,4-diF-benzyl-NH | 205–206 |
| 672 | " | " | " | " | " | 2-CF₃-benzyl-NH | 204–205 |

| | | | | | | |
|---|---|---|---|---|---|---|
| 673 | " | " | " | " | " | isobutyl-CH₂-NH- (3-methylbutylamine) | 164–165 |
| 674 | " | " | Cl | H | " | 2-(CF₃)-C₆H₄-CH₂-NH- | 270–280 |
| 675 | " | " | " | " | " | 3,4-diF-C₆H₃-CH₂-NH- | 288–290 |
| 676 | " | " | " | " | " | 3-(CF₃)-C₆H₄-CH₂-NH- | >260 |
| 677 | " | " | " | " | " | 2,4-diF-C₆H₃-CH₂-NH- | 265–270 |
| 678 | " | " | " | " | " | 4-F-C₆H₄-CH₂CH₂-NH- | >300 |
| 679 | " | " | " | " | " | 4-(CF₃)-C₆H₄-CH₂-NH- | 275–278 |
| 680 | " | " | " | " | " | 4-Cl-C₆H₄-CH₂-NH- | 297–300 |
| 681 | " | " | " | " | " | 2,4-diCl-C₆H₃-CH₂-NH- | >300 |
| 682 | CF₃ | H | H | OCH₃ | " | isobutyl-NH- | 232–233 |
| 683 | " | " | " | " | " | sec-butyl-NH- | 204–206 |
| 684 | " | " | " | " | " | isoamyl-NH- | 231–232 |
| 685 | " | " | " | " | " | C₆H₅-CH(CH₃)-CH₂-NH- | 189–190 |
| 686 | " | " | " | " | " | 4-Cl-C₆H₄-CH₂-NH- | 232–234 |

-continued

| No. | | | | | | Amine | mp |
|---|---|---|---|---|---|---|---|
| 687 | H | Cl | H | CF₃ | CH₃ | 3-NO₂-C₆H₄-CH₂-NH- | 204–206 |
| 688 | " | " | " | " | " | 3-Cl-C₆H₄-CH₂-NH- | 194–195 |
| 689 | " | " | " | " | " | 2-CH₃-C₆H₄-CH₂-NH- | 143–144 |
| 690 | " | " | " | " | " | 4-OCH₃-C₆H₄-CH₂-NH- | 166–168 |
| 691 | " | OCH₃ | " | OCH₃ | " | n-C₃H₇-NH- | 177–178 |
| 692 | " | " | " | " | " | iso-C₄H₉-NH- (isobutyl) | 178–180 |
| 693 | " | " | " | " | " | sec-C₄H₉-NH- | 226–228 |
| 694 | " | " | " | " | " | (CH₃)₂CHCH₂CH₂-NH- | 156–157 |
| 695 | " | " | " | " | " | C₆H₅-CH₂-NH- | — |
| 696 | " | " | " | " | " | 4-Cl-C₆H₄-CH₂-NH- | 233–234 |
| 697 | " | " | " | " | " | C₆H₅-CH(CH₃)CH₂-NH- | 140–141 |
| 698 | " | Cl | NO₂ | H | " | " | 235–237 |
| 699 | " | H | H | F | " | sec-C₄H₉-NH- | 116–118 |
| 700 | " | " | " | " | " | C₆H₅-CH(CH₃)CH₂-NH- | 121–123 |
| 701 | " | " | " | " | " | iso-C₄H₉-NH- | 98–100 |

| | | | | | | |
|---|---|---|---|---|---|---|
| 702 | " | morpholine (N-O ring) | " | H | " | phenylisopropylamine CH(CH3)CH2NH- | 79-80 |
| 703 | H | morpholine (N-O ring) | H | H | CH3 | CH3CH2NH- | 250-252 |
| 704 | " | " | " | " | " | CH3CH2CH(NH-)CH3 | 252-254 |
| 705 | Cl | Cl | " | Cl | " | CH3CH2CH2NH- | 140-142 |
| 706 | " | " | " | " | " | 2-methoxybenzyl-NH- | 231-233 |
| 707 | " | " | " | " | " | 4-chlorobenzyl-NH- | 237-239 |
| 708 | " | " | " | " | " | phenylisopropyl-NH- | 126-128 |
| 709 | " | " | " | " | " | isobutyl-NH- (3-methylbutyl) | 199-200 |
| 710 | " | " | " | " | " | sec-butyl-NH- | 144-145 |
| 711 | " | " | " | " | " | 2-methylcyclohexyl-NH- | 198-200 |
| 712 | " | " | " | " | " | isobutyl-NH- | 148-150 |
| 713 | " | " | " | " | " | 4-methylpiperazin-1-yl-NH- | 251-253 |
| 714 | " | " | " | " | " | benzyl-NH- | 205-207 |
| 715 | " | " | " | " | " | piperidin-1-yl-NH- | 261-263 |
| 716 | " | " | " | " | " | isopropyl-NH- | 218-219 |

| No. | | | | | | Structure | m.p. |
|---|---|---|---|---|---|---|---|
| 717 | H | " | H | H | C₆H₅ | HN-CH(CH₃)-CH₂-C₆H₅ | 285-286 |
| 718 | " | NO₂ | " | Cl | CH₃ | HN-CH₂-C₆H₅ | 155-157 |
| 719 | " | " | " | " | " | HN-CH₂-(2,4-Cl₂-C₆H₃) | 210-212 |
| 720 | " | " | " | " | " | HN-CH₂-(2-CH₃O-C₆H₄) | 88-90 |
| 721 | " | " | " | " | " | HN-CH₂-CH(CH₃)₂ | 166-168 |
| 722 | " | " | " | " | " | HN-N(piperidine) | 208-210 |
| 723 | H | H | H | H | C₆H₅ | HN-CH₂-(4-Cl-C₆H₄) | 293-294 |
| 724 | " | " | " | " | " | HN-N(piperidine) | 257-258 |
| 725 | " | " | " | " | " | HN-CH₂CH₂-(4-Cl-C₆H₄) | 295-296 |
| 726 | " | " | " | " | " | morpholine | >300 |
| 727 | " | " | " | " | " | HN-CH₂-CH(CH₃)₂ | 297-298 |
| 728 | " | " | " | " | " | HN-CH₂-CH₂-CH(CH₃)₂ | 238-240 |
| 729 | " | NO₂ | " | Cl | CH₃ | HN-N(4-methylpiperazine) | 219-220 |
| 730 | " | " | " | " | " | HN-CH(CH₃)₂ | 168-170 |

-continued

| No. | | | | | Amine | mp |
|---|---|---|---|---|---|---|
| 731 | " | H | " | H | C₆H₅ | 2-methoxybenzylamino (HN-CH₂-C₆H₄-OCH₃ ortho) | 293–294 |
| 732 | " | " | " | " | " | 4-methoxybenzylamino | 281–282 |
| 733 | " | " | " | " | " | sec-butylamino | 210–212 |
| 734 | " | " | " | " | " | n-propylamino | 187–188 |
| 735 | " | " | " | " | " | isopropylamino | 284–285 |
| 736 | " | Cl | Cl | Cl | CH₃ | isobutylamino | 145–147 |
| 737 | " | " | " | " | " | 1-phenylethylamino | 135–136 |
| 738 | " | H | H | F | " | benzylamino | 170–173 |
| 739 | " | " | " | " | " | isoamylamino | 110–112 |
| 740 | Cl | Cl | Cl | H | " | phenethylamino | >260 |
| 741 | " | " | " | " | " | isopropylamino | 166–168 |
| 742 | " | " | " | " | " | 3-phenylpropylamino | 220–222 |
| 743 | Cl | Cl | Cl | H | CH₃ | benzylamino | >260 |
| 744 | " | " | " | " | " | 4-methoxybenzylamino | 234–236 |
| 745 | " | " | " | " | " | isobutylamino | 250(dec) |

-continued

| No. | | | | | | Amine | mp |
|---|---|---|---|---|---|---|---|
| 746 | " | " | " | " | " | HN-CH2CH2CH(CH3)2 (isopentyl) | 154–156 |
| 747 | " | " | " | " | " | HN-propyl | 180(dec) |
| 748 | " | " | " | " | " | HN-sec-butyl | 226–228 |
| 749 | " | " | H | Cl | " | HN-CH2-(2,6-difluorophenyl) | 228–230 |
| 750 | " | " | " | " | " | HN-allyl | 204–206 |
| 751 | " | " | " | " | " | HN-CH2-(2,4-dichlorophenyl) | 246–247 |
| 752 | H | CH₃ | " | F | " | HN-isopropyl | 166–167 |
| 753 | " | " | " | " | " | HN-isobutyl | 123–125 |
| 754 | " | " | " | " | " | HN-CH2-(4-chlorophenyl) | 260–261 |
| 755 | " | " | " | " | " | HN-CH2-(2-methoxyphenyl) | 220–222 |
| 756 | " | " | " | " | " | HN-propyl | 127–129 |
| 757 | " | " | " | " | " | HN-(2-methylcyclohexyl) | 97–100 |
| 758 | " | " | " | " | " | HN-sec-butyl | 115–117 |
| 759 | " | " | " | " | " | HN-CH2-(4-methoxyphenyl) | 219–220 |
| 760 | " | F | " | CH₃ | " | HN-propyl | 136–137 |
| 761 | " | " | " | " | " | HN-isopropyl | oil |

-continued

| | | | | | | | |
|---|---|---|---|---|---|---|---|
| 762 | " | " | " | " | " | HN-CH2-CH(CH3)2 | 169-170 |
| 763 | " | " | " | " | " | HN-CH(CH3)-C2H5 | oil |
| 764 | " | " | " | " | " | HN-CH2-C6H5 | 174-176 |
| 765 | " | " | " | " | " | HN-CH2-C6H4-Cl | 203-204 |

| | | | | | | | |
|---|---|---|---|---|---|---|---|
| 766 | H | F | H | CH3 | CH3 | HN-CH2-C6H4-OCH3 | 209-210 |
| 767 | " | " | " | " | " | HN-cyclohexyl | 147-148 |
| 768 | " | " | " | " | " | HN-N(piperidine) | 154-155 |
| 769 | " | H | " | OC6H5 | " | HN-C2H5 | 163-165 |
| 770 | " | " | " | " | " | HN-CH(CH3)2 | 173-175 |
| 771 | " | " | " | " | " | HN-CH2-CH(CH3)2 | 177-179 |
| 772 | " | " | " | " | " | HN-CH(CH3)-C2H5 | 144-145 |
| 773 | " | " | " | " | " | HN-CH2-C6H5 | 202-204 |
| 774 | " | " | " | " | " | HN-CH2-C6H4-Cl | 165-167 |
| 775 | " | " | " | " | " | HN-CH2-C6H4-OCH3 | 182-184 |

| | | | | | | | |
|---|---|---|---|---|---|---|---|
| 776 | " | " | " | " | " | ![cyclohexyl-NH] | 135–136 |
| 777 | " | " | " | " | " | ![piperidinyl-NH-N] | 243–245 |
| 778 | NO₂ | " | " | Cl | " | ![HN-CH2-C6H4-OCH3] | 205–207 |
| 779 | H | Cl | " | CF₃ | C₆H₅ | ![HN-isobutyl] | 164–165 |
| 780 | " | " | " | " | " | ![HN-sec-butyl] | 194–195 |
| 781 | " | " | " | " | CH₃ | ![HN-CH2CH2-Cl] | 236–240 |
| 782 | NO₂ | H | " | Cl | " | " | 250–260 |
| 783 | " | " | " | " | " | ![HN-CH2CH2-Cl] | 200–202 |
| 784 | H | Cl | " | CF₃ | C₆H₅ | ![HN-propyl] | 132–133 |
| 785 | " | " | " | " | " | ![HN-CH2-C6H4-OCH3 ortho] | 154–155 |
| 786 | " | " | " | " | " | ![HN-isopropyl] | 222–223 |
| 787 | NO₂ | H | " | Cl | CH₃ | ![HN-CH2-CF3] | 230–233 |
| 788 | H | Cl | H | CF₃ | CH₃ | ![HN-CH2-CF3] | 169–170 |
| 789 | " | H | " | H | " | ![HN-C6H3(CF3)(Cl)] | 268–270 |
| 790 | " | " | Cl | Cl | " | ![HN-C6H4-Cl] | 213–215 |
| 791 | " | " | H | CF₃ | " | ![HN-C6H4-Br] | 225–227 |

-continued
| | | | | | | | |
|---|---|---|---|---|---|---|---|
| 792 | " | " | Cl | Cl | " | 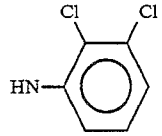 | 181-183 |
| 793 | " | " | " | " | " | 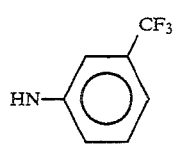 | 224-225 |
| 794 | " | " | " | " | " | 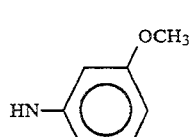 | 192-193 |
| 795 | " | " | " | " | " | 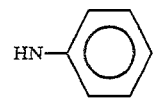 | 234-235 |
| 796 | " | " | " | " | " | 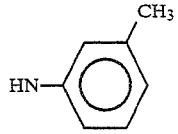 | 224-225 |
| 797 | " | " | " | " | " | 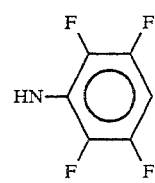 | 205-206 |
| 798 | " | " | " | " | " | 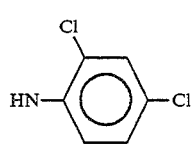 | 200-201 |
| 799 | " | " | " | " | " | 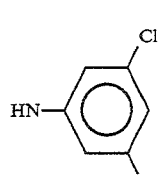 | 242-243 |
| 800 | " | " | " | " | " | 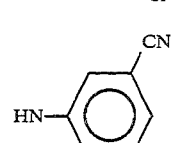 | 245-246 |
| 801 | " | Cl | H | CF$_3$ | " | 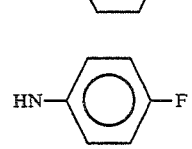 | 193-195 |
| 802 | " | " | " | " | " | 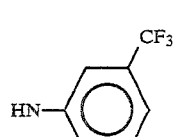 | 183-185 |

-continued

| No. | | | | | | Ar | mp |
|---|---|---|---|---|---|---|---|
| 803 | " | " | " | " | " | HN—C6H5 | 172–173 |
| 804 | " | " | " | " | " | HN—C6H4(3-OCH3) | 143–144 |
| 805 | " | " | " | " | " | HN—C6H3(2,3-Cl2) | 160–162 |
| 806 | " | " | " | " | " | HN—C6H3(3,5-Cl2) | 179–181 |
| 807 | " | " | " | " | " | HN—C6H4(2-Cl) | 171–173 |
| 808 | H | Cl | H | CF3 | CH3 | HN—C6H4(4-CF3) | 171–173 |
| 809 | " | " | " | " | " | HN—C6H3(2,4-Cl2) | 196–197 |
| 810 | " | " | " | " | " | HN—C6H4(4-Cl) | 222–224 |
| 811 | " | " | " | " | " | HN—C6H4(4-CH3) | 240–241 |
| 812 | " | " | " | " | " | HN—C6H3(2-CF3,4-Cl) | 212–213 |
| 813 | " | H | Cl | Cl | " | " | 215–217 |
| 814 | Cl | " | H | " | " | HN—C6H5 | 234–235 |
| 815 | " | " | " | " | " | HN—C6H4(4-F) | 224–225 |

-continued

| | | | | | | Structure | mp (°C) |
|---|---|---|---|---|---|---|---|
| 816 | " | " | " | " | " | HN—C₆H₄—Cl (4-Cl) | 208–209 |
| 817 | " | | " | " | " | HN—C₆H₃(2-Cl)(4-Cl) | 210–211 |
| 818 | " | " | " | " | " | HN—C₆H₄—CF₃ (4-CF₃) | 205–206 |
| 819 | " | " | " | " | " | HN—C₆H₄—CF₃ (3-CF₃) | 240–241 |
| 820 | " | " | " | " | " | HN—C₆H₄—F (3-F) | 263–265 |
| 821 | " | " | " | " | " | HN—C₆H₄—Cl (3-Cl) | 160–162 |
| 822 | " | " | " | " | " | HN—C₆H₄—Cl (2-Cl) | 210–211 |
| 823 | " | " | " | " | " | HN—C₆H₄—CH₃ (4-CH₃) | 160–162 |
| 824 | " | " | " | " | " | HN—C₆H₃(3-Cl)(5-Cl) | 243–245 |
| 825 | " | " | " | " | " | HN—C₆H₃(3-Cl)(4-Cl) | 268–270 |
| 826 | " | " | " | " | " | HN—C₆H₃(2-Cl)(3-Cl) | 250–252 |

| | | | | | | | |
|---|---|---|---|---|---|---|---|
| 827 | H | H | Cl | Cl | CH₃ | 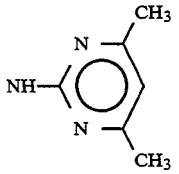 | 284–286 |
| 828 | " | " | " | " | " | 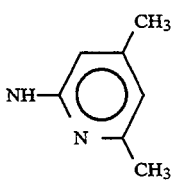 | >260 |
| 829 | " | " | " | " | " | 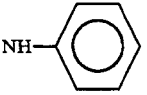 | 289–290 |
| 830 | " | CH₃ | H | " | " | 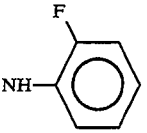 | 225–227 |
| 831 | " | " | " | " | " | 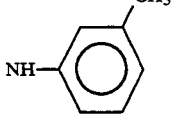 | 228–229 |
| 832 | " | " | " | " | " | 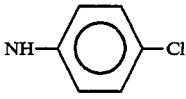 | 242–243 |
| 833 | " | " | " | " | " | 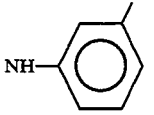 | 221–222 |
| 834 | " | " | " | " | " | 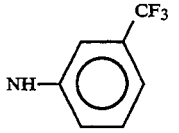 | >260 |
| 835 | " | " | " | " | " | 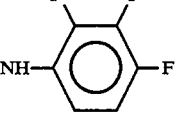 | 268–269 |
| 836 | " | Cl | " | CF₃ | " | 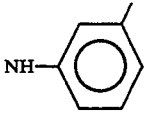 | 182–183 |
| 837 | " | " | " | " | " |  | 171–172 |

| | | | | | | |
|---|---|---|---|---|---|---|
| 838 | " | " | " | " | " | 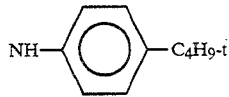 | 198–199 |
| 839 | " | " | " | " | " | 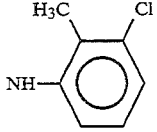 | 205–207 |
| 840 | " | " | " | " | " | 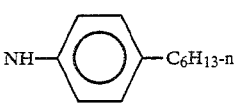 | 183–185 |
| 841 | " | " | " | " | " | 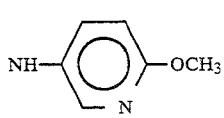 | 190–191 |
| 842 | " | " | " | " | " | 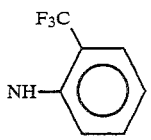 | 172–174 |
| 843 | " | " | " | " | " | 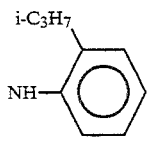 | 208–209 |
| 844 | " | " | " | " | " | 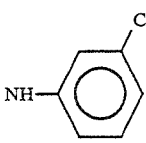 | 119–120 |
| 845 | " | " | " | Cl | " | 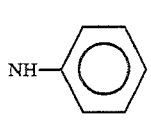 | 204–205 |
| 846 | " | " | " | " | " | 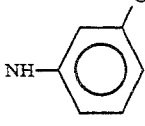 | 253–254 |
| 847 | " | " | " | " | " | 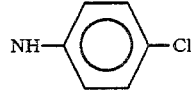 | 227–229 |
| 848 | " | " | " | " | " | 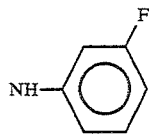 | 215–216 |
| 849 | " | " | " | " | " | 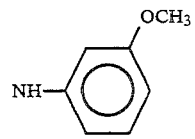 | 191–192 |

-continued
| | | | | | | |
|---|---|---|---|---|---|---|
| 850 | " | " | " | " | " | 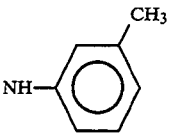 | 228–229 |
| 851 | " | " | " | " | " | 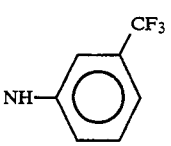 | 249–250 |
| 852 | H | Cl | H | Cl | CH₃ | 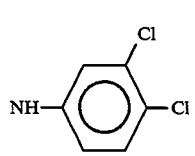 | 244–245 |
| 853 | " | " | " | CF₃ | C₂H₅ | 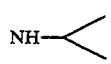 | 154–155 |
| 854 | " | " | " | CH₃ | CH₃ | 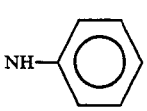 | 220–221 |
| 855 | " | " | " | " | " | 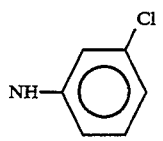 | >260 |
| 856 | " | " | " | " | " | 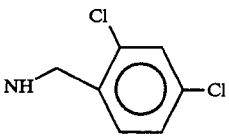 | 244–246 |
| 857 | " | " | " | " | " | 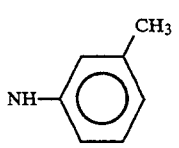 | 249–250 |
| 858 | " | " | " | " | " | 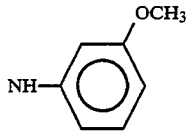 | 197–199 |
| 859 | " | " | " | " | " | 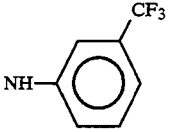 | >260 |
| 860 | " | " | " | " | " | 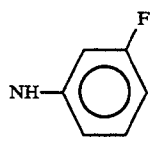 | 228–229 |
| 861 | " | H | " | C₂H₅ | " | 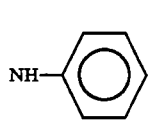 | 162–163 |

-continued
| | | | | | | | |
|---|---|---|---|---|---|---|---|
| 862 | " | " | " | " | " | 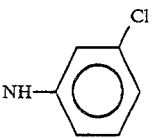 | 164–165 |
| 863 | " | " | " | " | " | 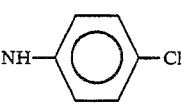 | 231–232 |
| 864 | " | " | " | " | " | 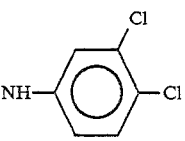 | 144–145 |
| 865 | " | " | " | " | " | 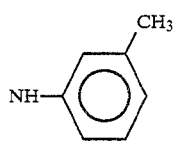 | 144–145 |
| 866 | " | " | " | " | " | 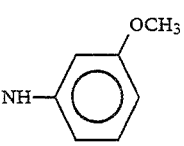 | 142–143 |
| 867 | " | " | " | " | " | 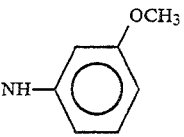 | 163–164 |
| 868 | " | " | " | " | " | 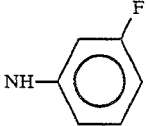 | 182–184 |
| 869 | " | Cl | " | $CF_3$ | $C_2H_5$ | 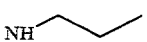 | 84–85 |
| 870 | " | H | " | " | $CH_3$ | 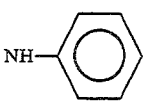 | 165–166 |
| 871 | " | " | " | " | " | 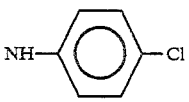 | — |
| 872 | " | " | " | " | " | 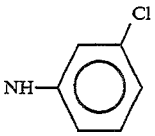 | 169–170 |
| 873 | " | " | " | " | " | 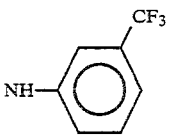 | 202–203 |

| | | | | | | | |
|---|---|---|---|---|---|---|---|
| 874 | " | " | " | " | " | 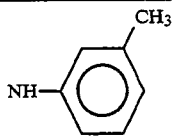 | 158–159 |
| 875 | " | " | " | " | " | 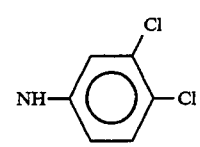 | 190–191 |
| 876 | " | " | " | " | " | 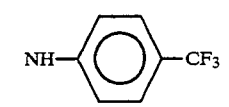 | 233–234 |
| 877 | " | " | " | " | " | 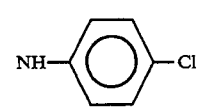 | 168–169 |
| 878 | H | H | H | CF$_3$ | CH$_3$ | 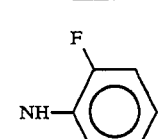 | 162–163 |
| 879 | " | F | " | CH$_3$ | " | 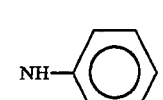 | 162–163 |
| 880 | " | " | " | " | " | 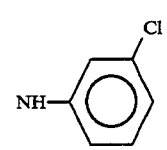 | 156–157 |
| 881 | " | " | " | " | " | 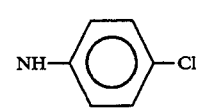 | 163–164 |
| 882 | " | " | " | " | " | 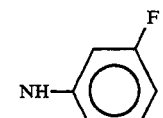 | 132–133 |
| 883 | " | " | " | " | " | 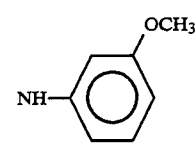 | 144–145 |
| 884 | " | " | " | " | " | 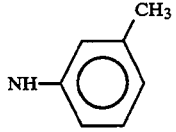 | 149–150 |
| 885 | " | " | " | " | " | 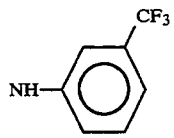 | 164–165 |

-continued

| | | | | | | |
|---|---|---|---|---|---|---|
| 886 | " | " | " | " | " | NH—C₆H₄—CF₃ (4-) | 169–170 |
| 887 | " | H | " | C₆H₅ | " | NH—C₆H₄—Cl (3-) | 167–168 |
| 888 | " | " | " | " | " | NH—C₆H₅ | 209–211 |
| 889 | " | " | " | " | " | NH—C₆H₄—Cl (4-) | 206–207 |
| 890 | " | " | " | " | " | NH—C₆H₄—Cl (3-) | 204–206 |
| 891 | " | " | " | " | " | NH—C₆H₄—CH₃ (3-) | 161–162 |
| 892 | " | " | " | " | " | NH—C₆H₄—OCH₃ (3-) | 183–186 |
| 893 | " | " | " | " | " | NH—C₆H₄—CF₃ (3-) | 174–176 |
| 894 | " | " | " | " | " | NH—C₆H₄—F (3-) | 190–192 |
| 895 | Cl | Cl | " | Cl | " | NH—C₆H₅ | 217–218 |
| 896 | " | " | " | " | " | NH—C₆H₄—CF₃ (3-) | 198–199 |
| 897 | " | " | " | " | " | NH—C₆H₄—F (3-) | 215–218 |

| | | | | | | |
|---|---|---|---|---|---|---|
| 898 | " | " | " | " | " | NH—C6H4—Cl (4-Cl) | 193–195 |
| 899 | " | " | " | " | " | NH—C6H4—Cl (3-Cl) | 282–285 |
| 900 | H | H | " | i-C3H7 | " | NH—C6H4—CF3 (3-CF3) | 186–189 |
| 901 | " | " | " | CH2C6H5 | " | NH—C6H4—F (3-F) | 110–114 |
| 902 | " | " | " | " | " | NH—C6H5 | 156–157 |
| 903 | " | " | " | " | " | NH—C6H4—CF3 (3-CF3) | 199–200 |
| 904 | H | H | H | CH2C6H5 | CH3 | NH—C6H3(Cl)2 (2,4-Cl2) | 128–130 |
| 905 | NO2 | " | " | Cl | " | NH—C6H4—CF3 (4-CF3) | 238–239 |
| 906 | " | " | " | " | " | NH—C6H4—CF3 (3-CF3) | 267–268 |
| 907 | " | " | " | " | " | NH—C6H3(Cl)2 (3,4-Cl2) | 210–213 |
| 908 | " | " | " | " | " | NH—C6H4—Cl (4-Cl) | 240–242 |
| 909 | " | " | " | " | " | NH—C6H4—Cl (3-Cl) | 180–182 |

-continued

| | | | | | | | |
|---|---|---|---|---|---|---|---|
| 910 | " | " | " | " | " | NH—C₆H₄—CH₃ (3-methyl) | 217–219 |
| 911 | " | " | " | " | " | NH—C₆H₄—F (3-F) | 293–295 |
| 912 | " | " | " | " | " | NH—C₆H₄—OCH₃ (3-OCH₃) | 228–230 |
| 913 | H | " | Cl | " | " | NH—C₆H₄—Br (4-Br) | 224–225 |
| 914 | " | " | " | " | " | NH—C₆H₄—Cl (3-Cl) | 216–217 |
| 915 | " | " | " | " | " | NH—C₆H₄—Cl (3-Cl) | 222–223 |
| 916 | " | " | " | " | " | NH—C₆H₄—F (4-F) | 204–205 |
| 917 | " | " | " | " | " | NH—C₆H₅ | 262–263 |
| 918 | " | " | " | " | " | NH—C₆H₄—Cl (3-Cl) | 271–274 |
| 919 | " | " | " | " | " | NH—C₆H₄—Cl (4-Cl) | 254–256 |
| 920 | " | " | " | " | " | NH—C₆H₃—Cl₂ (2,4-Cl₂) | >260 |
| 921 | " | " | " | " | " | NH—C₆H₃—Cl₂ (3,4-Cl₂) | >260 |

| | | | | | | |
|---|---|---|---|---|---|---|
| 922 | " | " | " | " | " | ![3-methylanilino]  NH—C6H4—CH3 (meta) | 260–261 |
| 923 | " | " | " | " | " | NH—C6H4—OCH3 (meta) | 228–230 |
| 924 | " | " | " | " | " | NH—C6H4—CF3 (meta) | >260 |
| 925 | " | " | " | " | " | NH—C6H4—CF3 (para) | >300 |
| 926 | " | " | " | " | " | NH—C6H4—F (meta) | 240–242 |
| 927 | " | " | " | Cl | " | NH—CH2—CF3 | 232–233 |
| 928 | " | Cl | H | CF3 | C2H5 | " | 113–115 |
| 929 | " | H | " | " | CH3 | " | 151–152 |
| 930 | Cl | Cl | Cl | H | CH3 | NH—CH2—CF3 | 272–273 |
| 931 | H | F | H | CF3 | " | " | 156–157 |
| 932 | " | " | " | " | " | NH—CH(CH3)2 | 125–130 |
| 933 | " | " | " | " | " | NH—CH2CH2CH3 | 160–161 |
| 934 | " | H | " | F | " | NH—C6H5 | 209–210 |
| 935 | " | " | " | " | " | NH—C6H4—CF3 (ortho) | 219–220 |
| 936 | " | " | Cl | Cl | C2H5 | NH—CH2—CF3 | 238–239 |
| 937 | " | Cl | H | CF3 | n-C3H7 | " | 159–160 |
| 938 | " | " | " | " | " | NH—C6H3(Cl)2 (3,5-dichloro) | 165–167 |

-continued

| No. | | | | | | | mp |
|---|---|---|---|---|---|---|---|
| 939 | " | " | " | " | " | NH—CH(CH3)2 | — |
| 940 | " | " | " | " | CH3 | [triazole]-NH | >260 |
| 941 | " | H | " | " | " | [triazole]-NH | >260 |
| 942 | " | " | " | " | i-C3H7 | NH—CH(CH3)2 | 103–104 |
| 943 | " | " | " | " | " | NH—C6H4—Cl | 130–131 |
| 944 | " | Cl | " | " | " | NH—CH(CH3)2 | 129–130 |
| 945 | " | " | " | " | " | NH—CH2—C6H4—Cl | 163–164 |
| 946 | " | " | " | " | " | NH—CH2—CF3 | 119–121 |
| 947 | " | " | " | " | " | " | 98–100 |
| 948 | " | " | " | " | i-C4H9 | NH—CH2—C6H4—Cl | 144–146 |
| 949 | " | " | " | " | " | NH—CH(CH3)2 | 134–137 |
| 950 | " | H | F | CH3 | CH3 | " | 211–213 |
| 951 | " | " | " | " | " | NH—CH2—C6H3(Cl)2 | 208–210 |
| 952 | " | " | " | " | " | NH—CH2—CF3 | 237–238 |
| 953 | Cl | " | H | " | | NH—CH(CH3)2 | — |

EXAMPLE 1

3-Acetyl-4-methylthio-2-quinolinone (1)

N-Phenyl-α-(bismethylthioylidene)acetoacetamide(28.1 g, 0.1 mol) was heated and refluxed for 2hr in solvent of dichlorobenzene(300 ml) untill the evolution of methylmercaptane ceased.

The reaction progress was determined by chromatography. When the reaction was completed, the reaction mixture was cooled, and then the precipitate was filtered to give the desired product( 19.1 g, yield: 82 % ).

$^1$H NMR ( DMSO-d$_6$): δ10.7(s, 1H),8.2~7.15(m,4H),2.65(s,3H),2.53(s,3H).

EXAMPLE 2

3-Acetyl-7-methoxy-4-methylthio-2-quinolinone (2)

N-(m-Anisyl)-α-(bismethylthioylidene)acetoacetamide(3.1 g, 0.01 mol) was used, but the reaction was carried out as the above process of example 1 to obtain the desired product(2.1g, yield: 82%).

¹H NMR(CDCl₃): δ10.49(s, 1H), 8.18~6.68(s, 3H), 3.8(s, 3H), 2.64(s, 3H), 2.53(s, 3H).

EXAMPLE 3

3-Acetyl-8-chloro-4-methylthio-2-quinolinone (3)

N-(2-Chlorophenyl)-α-(bismethylthioylidene)acetoacetamide (3.2g, 0.01 mol) was used, but the reaction was carried out as the above process of example 1 to obtain the desired product (2.2g, yield: 86%).

¹H NMR (DMSO-d₆ ): δ8.2~7.25(m, 3H), 4.5~3.0(brs), 2.67(s, 3H), 2.59(s, 3H).

EXAMPLE 4

3-Acetyl-5,8-dichloro-4-methylthio-2-quinolinone (4)

N-(2,5-Dichlorophenyl)-α-(bismethylthioylidene)acetoacetamide (3.5g, 0.01 mol) was used, but the reaction was carried out as the above process of example 1 to obtain the desired product (2.0g, yield:68%).

¹H NMR(DMSO-d₆, +CDCl₃): δ7.7 (d, J=9.0, 1H),7.27(d, J=9.0, 1H), 2.64(s,3H), 2.52(s,3H).

EXAMPLE 5

3-Acetyl-6-methoxy-4-methylthio-2-quinolinone (5)

N-(p-Anisyl)-α-(bismethylthioylidene)acetoacetamide (3.1 g, 0.01 mol) was used, but the reaction was camm out as the above process of example 1 to obtain the desired product (1.9g, yield: 74%).

¹H NMR(DMSO-d₆): δ10.68(s,1H),7.93~6.95(m,3H),3.83(s,3H), 2.63(s,3H),2.59(s,3H).

EXAMPLE 6

3-Acetyl-6-fluoro-4-methylthio-2-quinolinone (7)

N-(4-Fluorophenyl)-α-(bismethylthioylidene)acetoacetamide (3.0g, 0.01 mol) was used, but the reaction was carried out as the above process of example 1 to obtain the desired product (2.3g, yield: 95%).

¹H NMR(DMSO-d₆+CDCl3): δ8.1~7.2(m,3H),2.62(s,3H), 2.55(s, 3H). EXAMPLE 7

3-Acetyl-8-fluoro-4-methylthio-2-quinolinone (8)

N-(2-Fluorophenyl)-α-(bismeth ylthioylidene)-butyrylacetami de (3.0g, 0.01 mol) was used, but the reaction was carried out as the above process of example 1 to obtain the desired product (2.0g, yield: 85%).

¹H NMR( DMSO-d₆+CDCl₃): δ6.13~7.1(m,3H),2.65(s,3H),2.57(s,3H).

EXAMPLE 8

3-Butyryl-8-chloro-4-methylthio-2-quinolinone (9)

N-(2-Chlorophenyl)-α-(bismethyl thioylidene)-butyrylacetamide (3.4g, 0.01 mol) was used, but the reaction was carded out as the above process of example 1 to obtain the desired product (2.5g, yield: 895).

¹H NMR(CDCl₃): δ8.7(s,1H), 8.52~8.05(m,1H),7.47~6.75(m,3H), 2.760, (t,J=7.0, 2H),2.45(s,6H), 1.72(m,2H), 2.45(s,6H), 1.72(m,2H), 0.95(t,J=7.0, 3H).

EXAMPLE 9

3-Acetyl-8-methyl-8-methylthio-2-quinolinone (11)

N-(o-Tolyl)-α-(bismethyl thioylidene)acetoacetamide (3.0g, 0.01 mol) was used, but the reaction was carried out as the above process of example 1 to obtain the desired product (2.1g, yield: 88%).

¹H NMR(DMSO-d₆): δ15.6(s,1H), 8.06~7.3(m,3H),2.93(s,3H), 2.69(s, 3H), 2.65(s,3H).

EXAMPLE 10

3-Benzoyl-8-chloro-4-methylthio-2-quinolinone (12)

N-(2-Chlorophenyl)-α-(bismethylthioylidene) benzoylacetamide (3.8g, 0.01 mol) was used, but the reaction was carried out as the above process of example 1 to obtain the desired product (2.6g, yield : 81%).

¹H NMR(DMSO-d₆, CDCl₃): δ8.3~7.2(m,8H),2.65(s,3H).

EXAMPLE 11

3-Acetyl-6-chloro-8-trifluoroethy14-methylthio-2-quinolinone (13)

N-( 4-Chloro-2-trifluoromethylphenyl)-α-(bismethylthioylidene) acetoacetamide (3.8 g, 0.01 mol) was used, but the reaction was carded out as the above process of example 1 to obtain the desired product (2.3g, yield: 71%).

¹H NMR( CDCl₃+DMSO-d₆ ): δ8.3(s,1H), 8.12(s,3H), 2.67(s,3H).

EXAMPLE 12

3-Acetyl-8-methoxycarbonyl-4-methylthio-2-quinolinone (16)

N -(2-Methoxycarbonylphenyl)- α-(bismethylthioylidene)acetoacetamide (3.4g, 0.01 mol) was used, but the reaction was carried out as the above process of example 1 to obtain the desired product (2.8g, yield: 99%).

¹H NMR(DMSO-d₆+CDCl₃): δ2.6(s,3H), 3.27(s,3H), 4.03(s,3H), 7.4~8.6(m,3H).

EXAMPLE 13

3-Acetyl-6-nitro-4-methylthio-2-quinolinone (20)

N-(4-Nitrophenyl)-α-(bismethylthioylidene)acetoacetamide (3.3g, 0.01 mol) was used, but the reaction was carried out as the above process of example 1 to obtain the desired product (2.1 g, yield: 80% ).

¹H NMR(DMSO-d₆+CDCl₃): δ2.57(s,3H), 2.66(s,3H),8.0~8.9(m,4H).

EXAMPLE 14

3-Acetyl-6-chloro-7-nitro-4-methylthio-2-quinolinone (21)

N-(3-Nitro-4-chlorophenyl)-α-(bismethyl thioylidene)acetoacemmide (3.6g, 0.01 mol) was used, but the reaction was carded out as the above process of example to obtain the desired product (1.8g, yield: 61%).

¹H NMR(DMSO-d₆+CDCl₃): δ2.43(s,3H), 2.7(s,3H), 7.73~8.13(m,2H), 11.4(s,1H).

EXAMPLE 15

3-Acetyl-8-cyano-4-methylthio-2-quinolinone(22)

N-(2-Cyanophenyl)-α-(bismethylthioylidene)acetoacetamide (3.1g, 0.01 mol) was used, but the reaction was carried out as the above process of example 1 to obtain the desired product (1 .8g, yield: 73%).

$^1$H NMR(DMSO-d$_6$+CDCl$_3$): δ2.13(s,3H), 2.7(s,3H), 7.6~8.7(m,3H).

EXAMPLE 16

3-Acetyl-6-chloro-8-trifluoromethyl-4-(t-butylbenzylthio)-2-quinolinone (23)

N-( 4-Chloro-2-trifluo romet hylph enyl) -α-[bis-(t-butylbenzylthio)ylidene]acetoacetamide (6.3g, 0.01 mol) was used, but the reaction was carded out as the above process of example 1 to obtain the desired product (2.5g, yield: 54%).

$^1$H NMR(DMSO-d$_6$+CDCl$_3$): δ1.27(s,9H), 2.73(s,3H), 4.6(s,2H), 7.35(s,4H), 7.95(d,1H), 8.52(d,1H).

EXAMPLE 17

3-Acetyl-6-t-butyl-4-methylthio-2-quinolinone (24)

N-(4-t-Butylphenyl)-α-(bismethylthioylidene)acetoacetamide (3.4g, 0.01 mol) was used, but the reaction was carried out as the above process of example 1 to obtain the desired product (2.3g, yield: 84%).

$^1$H NMR(DMSO-d$_6$+CDCl$_3$): δ1.37(s,9H), 2.6(s,3H), 2.63(s,3H), 7.73(d,2H), 8.23(s,1H), 10.83(s,1H).

EXAMPLE 18

3-Acetyl-5,6,7,8-tetrachloro-4-methylthio-2-quinolinone (27)

N-(2,3,4,5-Tetrachlorophenyl)-α-(bismethylthioylidene)acetoacetamide (3.5g, 0.01 mol) was used, but the reaction was carried out as the above process of example 1 to obtain the desired product (2.6g, yield: 74%).

$^1$H NMR(DMSO-d$_6$+CDCl$_3$): δ2.43(s,3H), 2.66(s,3H), 7.96(s,1H).

EXAMPLE 19

3-Acetyl-8-trifluommethyl-4-methylthio-2-quinolinone (29)

N-(2-Tfifiuoromethylphenyl)-α-(bismethylthioylidene)acetoacetamide (3.5 g, 0.01mol) was used, but the reaction was carried out as the above process of example to obtain the desired product (1 .9g, yield: 65%).

$^1$H NMR(DMSO-d$_6$+CDCl$_3$): δ2.6(s,3H), 2.7(s,3H), 8.06(m,1H),8.63(m,1H).

EXAMPLE 20

3-Acetyl-8-fluoro-8-trifluoromethyl-4-methylthio-2-quinolinone (33)

N-(4-Fluoro-2-trifluoromethylphenyl)-α-(bismethylthioylidene)acetoacet amide (3.7g, 0.01 mol) was used, but the reaction was carried out as the above process of example 1 to obtain the desired product (2.5g, yield: 83%).

$^1$H NMR(CDCl$_3$): δ2.7(s,3H), 2.97(s,3H), 7.73~8.16(m,1H), 15.63(s,1H).

EXAMPLE 21

3-Acetyl-7-fluoro-8-trifluoromethyl-4-methylthio-2-quinolinone (34)

N-(2 -Trifluoromethyl-3 -fluorophenyl)-α- (bismethylthioylidene)acetoacet amide (3.7g, 0.01 mol) was used, but the reaction was carried out as the above process of example 1 to obtain the desired product (2.2g, yield: 73%).

$^1$H NMR(CDCl$_3$): δ2.72(s,3H), 2.93(s,3H), 7.1~7.68(m,1H), 7.83~8.1(m,2H).

EXAMPLE 22

3-Acetyl-6-bromo-8-trifluoromethyl-4-methylthio-2-quinolinone (35)

N-4-Bromo-8-trifluoromethyl-α-(bismethylthioylidene)acetoacetarnide (4.3g, 0.01 mol) was used, but the reaction was carried out as the above process of example to obtain the desired product (2.5g, yield: 67%).

$^1$H NMR(CDCl$_3$): δ2.7(s,3H), 2.93(s,3H), 8.1(s,1H), 8.53(s,1H), 15.6(s,1H).

EXAMPLE 23

3-Acetyl-6-chloro-7-trifluoromethyl-4-methylthio-2-quinolinone (36)

N-(3-Trifluoromethyl)-α-(bismeth ylthioylidene)acetoacetamide (3.8g, 0.01 mol) was used, but the reaction was carried out as the above process of example 1 to obtain the desired product (1 .7g, yield: 52%).

$^1$H NMR(CDCl$_3$): δ2.7(s,3H), 2.92(s,3H), 8.1~8.3(m,2H), 15.57(s,1H).

EXAMPLE 24

3-Acetyl-6-hexyl-4-methylthio-2-quinolinone (37)

N-4-Hexylphenyl)-α-(bismethylthioylidene)acetoacetamide (3.7 g, 0.01 mol) was used, but the reaction was carried out as the above process of example 1 to obtain the desired product (2.5g, yield: 82%).

$^1$H NMR(CDCl$_3$): δ0.78~0.97(m,3H), 1.16~1.8(m,10H), 2.67(s,3H), 2.83(s,3H), 7.57~8.07(m,3H).

EXAMPLE 25

3-Acetyl-6,7,8-trifluoro-4-methylthio-2-quinolinone (38)

N-(2,3,4-Trifluorophenyl)-α-(bismethylthi oylidene)acetoacetamide (3.4g, 0.01 mol) was used, but the reaction was carried out as the above process of example 1 to obtain the desired product (1.8g, yield: 67%).

$^1$H NMR(CDCl$_3$): δ2.73(s,3H), 2.97(s,3H), 7.6~7.93(m,1H), 15.73(s,1H).

EXAMPLE 26

3-Acetyl-6-chloro-8-trifluoromethyl-4-(2,4-dichlorobenzylthio)-2-quinolinone (39)

N-(4-Chloro- 2-trifluoromethylphenyl)-α-[bis(2,4-dichlorobenzylthio) ylidene]-acetoacetamide (6.0g, 0.01 mol) was used, but the reaction was carried out as the above process of example 1 to obtain the desired product (2.4g, yield: 51%).

$^1$H NMR(CDCl$_3$): δ15.68(s,1H), 8.57(m,1H), 8.17(m,1H), 7.67~7.03(m,4H), 4.87(s,2H), 2.97(s,3H).

EXAMPLE 27

3-Acetyl-8-chloro4-methylsulfoxy-2-quinolinone (91)

3-Acetyl-8-chloro-4-methylthio-2-quinolinone (26.7g, 0.1 mol)(3) was dissolved in 200 ml of ethyl alcohol, and herein the solution of magnesium monoperoxyphthalate (29.1g, 0.1 mol)dissolved in 150 ml of water was added dropwise at room temperature.

After raising the reaction temperature to 50° C., the reacting solution was maintained for 2hr, and then ethyl alcohol was evaporated and 500 ml water was added.

The obtained solid w as filtered and recrystallized in 100 ml of ethyl alcohol to afford the desired product (23.2g, yield: 82%).

$^1$H NMR(CDCl$_3$): δ8.3~7.5(m,3H), 3.1(s,3H), 2.8(s,3H).

EXAMPLE 28

3-Acetyl-6-methoxy-4-methylsulfoxy-2-quinolinone (92)

3-Acetyl-6-methoxy-4-methylthio-2-quinolinone (2.6g, 0.01 mol)(5) was dissolved in 10ml of acetic acid, and the solution was stirred at 80° C., and herein hydrogen peroxide (30% solution 2.83g, 0.025 mol) was added dropwise and stirred for 30min at 80° C.

After reacting under the above conditions, the solution was cooled and poured in 500g of ice water, and then the deposited solid was filtered and dried to obtain the desired product (2.3g, yield: 85%).

$^1$H NMR(CDCl$_3$): δ8 7.9~7.3(m,3H), 3.9(s,3H), 3.0(s,3H), 2.8(s,3H).

EXAMPLE 29

3-Acetyl-5,8-dichloro-4-methylsulfoxy-2-quinolinone (93)

3-Acetyl-5,8-dichloro-4-methylthio-2-quinolinone (3.0g, 0.01 mol)(4) was used, but the reaction was carried out as the above process of example 27 to obtain the desired product (2.4g, yield: 78%).

$^1$H NMR(CDCl$_3$): δ8.0~7.0(m,2H), 3.1(s,3H), 2.75(s,3H).

EXAMPLE 30

3-Acetyl-8-fluoro4-methylsulfoxy-2-quinolinone (97)

3-Acetyl-8-fluoro-4-methylthio-2-quinolinone (2.5g, 0.01 mol)(8) was used, but the reaction was carried out as the above process of example 27 to obtain the desired product (2.0g, yield: 79%).

$^1$H NMR(CDCl$_3$): δ8.3~7(m,4H), 3.05(s,3H), 2.82(s,3H).

EXAMPLE 31

3-Acetyl-6-chloro-8-trifluoromethyl-4-methylsulfoxy-2-quinolinone (98)

3-Acetyl-6-chloro-8-trifluoromethyl-4-methylthio-2-quinolinone (3.4g, 0.01 mol)(13) was used, but the reactiota was carried out as the above process of example 27 to obtain the desired product (2.9g, yield: 85%).

$^1$H NMR(CDCl$_3$): δ2.75(s,3H), 3.0(s,3H), 8.6(d,1H), 8.0(d,1H), 11.25(s,1H).

EXAMPLE 32

3-Acetyl-4-benzylsulfoxy-8-fluoro-2-quinolinone (100)

3-Acetyl-4-benzylthio-8-fluoro-2-quinolinone (3.2g, 0.01 mol)(15) was used, but the reaction was carried out as the above process of example 27 to obtain the desired product (2.9g, yield: 87%).

$^1$H NMR(CDCl$_3$): δ2.86(s,3H), 4.37(s,2H), 7.13~7.47(m,8H), 8.16(s,1H).

EXAMPLE 33

3-Acetyl-8-trifluoromethyl-4-methylsulfoxy-2-quinolinone (102)

3-Acetyl-8-trifluoromethyl-4-methylthio-2-quinolin one (3.0 g, 0.01 mol)(29 ) was used, but the reaction was camed out as the above process of example 27 to obtain the desired product (2.5g, yield: 82%).

$^1$H NMR(CDCl$_3$): 2.87(s,3H), 3.03(s,3H), 7.52~8.78(m,3H), 11.25(s,1H)

EXAMPLE 34

3-Acetyl-8-cyano-4-methylsulfoxy-2-quinolinone (104)

3-Acetyl-8-cyano-4-methylthio-2-quinolinone (2.6g, 0.01 mol)(29) was used, but the reaction was carded out as the above process of example 27 to obtain the desired product (1.8g, yield: 68%).

$^1$H NMR(CDCl$_3$): δ2.67(s,3H), 7.6~8.67(m,4H).

EXAMPLE 35

3-Acetyl-5,8-dichloro- 4-(p-chloro phenyl)thio-2-quinolinone (182)

3-Acetyl-5,8-dichloro-4-methylsulfoxy-2-quinolinone (3.2g, 0.01 mol)(93 ) and p-chlorothiophenol(1.73g, 0.012 mol) were stirred at 20° C., heated for 30 min, slowly cooled to 100° C., and dissolved in 15ml of toluene.

After cooling to room temperature, the deposited crystal was filtered and dried to obtain the desired product (3.3g, yield: 83%).

$^1$H NMR(CDCl$_3$): 7.2~8.3(m,6H), 3.00(s,3H).

EXAMPLE 36

3-Acetyl-5,8-dichloro-4-(p-chlorophenyl)sulfoxy-2-quinolinone (184)

3 -Acetyl-5,8-dichloro-4- (p-chlorophenyl)thio-2-quinolinone (1 g, 0.0025 mol) (182) was dissolved in the mixture of 5 ml of acetic acid and hydrogen peroxide (30% solution 0.57g, 0.005 mol), and stirred for 30 min at 100° C.

The solution was poured in 50g of ice water, and then the deposited solid was filtered and dried to obtain the desired product (0.8g, yield: 73%).

$^1$H NMR(DMSOd$_6$-CDCl$_3$): δ7.2~8.3(m,6H), 3.05(s,3H).

EXAMPLE 37

3-Acetyl-6-chloro-8-trifluoromethyl-4-(2-phenylethylamino)-2-quinolinone (223)

3-Acetyl-6-chloro-8-trifluoromethyl-4-methylsulfoxy-2-quinolinone (3.5g, 0.01 mol) and 2-phenylethylamine(1.21g, 0.01 mol) were dissolved, refluxed in 50ml of tetrahydrofuran under heating for 4hr.

After reacting, the solvent was evaporated under the reduced pressure, and then the obtained solid was dissolved in 10ml of ethylacetate under heating.

The solution was recrystallized with adding 30ml of hexane to obtain the desired product (2.57g, yield: 73%).

$^1$H NMR (CDCl$_3$): δ11.78(brs, 1H), 8.47(d, J=2.0, 1H), 7.75(d, J=2.0, 1H), 7.75(brs, 1H), 7.33(s,5H), 3.55(m,2H), 3.08(m,2H), 2.7(s,3H).

EXAMPLE 38

3-Acetyl-6-chloro-8-trifluoromethyl-4-isopropylamino-2-quinolinone (224)

3-Acetyl-6-chloro-8-tfifluoromethyl-4-methylsulfoxy-2-quinolinone (3.5g, 0.01 mol)(13) and isopropylamine (0.6g, 0.01 mol) were used, but the reaction was carried out as the above process of example 37 to obtain the desired product (2.52g, yield: 73%).

$^1$H NMR (CDCl$_3$): δ11.7(s,1H), 8.58(m,1H), 7.87(m,1H), 3.77(m,J =6.5, 1H), 2.93(s,3H), 1.47(d, J=6.5, 6H).

EXAMPLE 39

3-Acetyl-6-chloro-8-trifiuoromethy-4-cyclopentylamino-2-quinolinone (227)

3-Acetyl-6-chloro-8-trifluoromethyl-4-methylsulfoxy-2-quinolinone (3.5g, 0.01 mol) and cyclopentylamine (0.86g, 0.01 mol) were used, but the reaction was carried out as the above process of example 37 to obtain the desired product (2.5g, yield: 67 % ).

$^1$H NMR (CDCl$_3$): δ11.8(brs, 1H), 8.47(m,1H), 7.83(brs, 1H), 7.77(m,1H), 3.85(brs, 1H), 2.73(s,3H), 2.47~1.38(m,8H).

EXAMPLE 40

8-Chloro-3-propionyl-4-isopropylamino-2-quinolinone (229)

8-Chloro-4-methylsulfoxy-3-propionyl-2-quinolinone (2.97g, 0.01 mol) and isopmpylamine (0.6g, 0.01 mol) were used, but the reaction was carried out as the above process of example 37 to obtain the desired product (2.93g, yield: 71% ).

$^1$HNMR (CDCl$_1$): δ11.78(br,1H), 8.4~6.97(m,4H), 3.87(m,J=7.0, 1H), 3.27(q,J=8.0, 2H), 1.65(d, J=7.0, 6H), 1.17(t, J=8.0, 3H).

EXAMPLE 41

3-Acetyl-8-methyl-4-isopropylamino-2-quinolinone (230)

3-Acetyl-8-methyl-4-methylsulfoxy-2-quinolinone (2.63g, 0.01 mol) and isopropylamine (0.6g, 0.01 mol) were used, but the reaction was carded out as the above process of example 37 to obtain the desired product (2.59g, yield: 68%).

$^1$H NMR (DMSO-d6): δ11.5(br. d, 1H), 8.33~7.23(m,4H), 3.8(m, J=7.0, 1H), 2.77(s,3H), 2.4(s,3H), 1.45(d,J=7.0,6H).

EXAMPLE 42

3-Acetyl-6-chloro-8-trifluoromethyl-4-(p-fluorophenethyl amino)-2-quinolinone (227)

3-Acetyl-6-chloro-8-trifluoromethyl-4-methylsul foxy-2-quinolinone (3.5g, 0.01 mol), p-fluorophenethylamine hydrochloride(1.76g, 0.01 mol) and triethylamine (1.1g, 0.01 mol) were used as the above process of example 37, and the solvent was evaporated under the reduced pressure.

The residue was dissolved in 50 ml of ethylacetate, washed with 50 ml of water, dried with magnessium sulfate, and then the solvent was evaporated.

The obtained solid was dissolved in 10 ml of ethyl acetate, and crystallized by adding 30 ml of hexane to afford the desired product (2.25g, yield: 53%).

$^1$H NMR (CDCl$_3$): δ2.7(s,3H), 2.97~3.16(t,J=6.4, 2H), 3.47~3.77(m,2H), 6.93~8.47(m,7H), 11.73(s,1H).

EXAMPLE 43

3-Acetyl-8-fluoro-4-(1-methoxy-2-propylamino)-2-quinolinone (249)

3-Acetyl-8-fluoro-4-methylsulfoxy-2-quinolinone (2.67g, 0.01 mol) and 1-methoxy-2-propylamine(0.88g, 0.01 mol) were used, but the reaction was carried out as the above process of example 37 to obtain the desired product (2.53g, yield: 87%).

$^1$H NMR (CDCl$_3$): δ1.5(d,3H), 2.8(s,3H), 3.7~3.9(m,3H), 3.6(s,3H), 7.2~8.3(m, 4H).

EXAMPLE 44

3-Acetyl-6-chloro-8-trifluoromethyl-4-ethylamino-2-quinolinone (251)

3-Acetyl-6-chloro-8-trifluoromethyl-4-methylsulfoxy-2-quinolinone (3.5g, 0.01 mol) and ethylamine(70 wt % solution; 0.65g, 0.01 mol) were used, but the reaction was carried out as the above process of example 37 to obtain the desired product (2.52g, yield: 76%).

$^1$H NMR (CDCl$_3$): δ1.37~1.6(t,J=8, 3H), 2.73(s,3H), 3.23~3.67(m,2H), 7.77~8.47(m,3H), 11.57(s,1H).

EXAMPLE 45

3-Acetyl-8-fluoro-4-(2-methyl cyclohexylamino)-2-quinolinone (256)

3-Acetyl-8-fiuoro-4-methylsulfoxy-2-quinolinone (2.67g, 0.01 mol) and 2methylcyclohexylamine(1.13g, 0.01 mol) were used, but the reaction was carried out as the above process of example 37 to obtain the desired product (2.1g, yield: 66%).

$^1$H NMR (CDCl$_3$): δ1.0~1.5(m,12H), 2.6(s,3H), 3.9(m,1H), 7.1~8.4(m,3H).

EXAMPLE 46

3-Acetyl-8-trifluoromethyl-4-(a-methylbenzylamino)-2-quinolinone (260)

3-Acetyl-8-trifluoromethyl-4-methylsulfoxy-2-quinolinone (3.17 g, 0.01 mol) and α-methylbenzylamine (1.21 g, 0.01 mol) were used, but the reaction was carried out as the above process of example 37 to obtain the desired product (2.43g, yield: 65%).

$^1$H NMR (CDCl$_3$): δ1.63~1.83 (d,J=7, 3H), 2.8(s,3H), 4.57~4.77(m,1H), 7.23~8.6(m,9H), 12.2(s,1H).

EXAMPLE 47

3-Acetyl-8-chloro-4-(p-chlorobenzylamino)-5-nitro-2-quinolinone (308)

3-Acetyl-8-chloro-4-methylsulfoxy-5-nitro-2-quinolinone (3.28g, 0.01 mol ) and p-chlorobenzylamine (1.42g, 0.01 mol) were used, but the reaction was carried out as the above process of example 37 to obtain the desired product (2.32g, yield: 57%).

$^1$H NMR (DMSO-d$_6$): δ8 11.9(m,1H), 8.43(brs, 1H), 7.8(d,J=9.0, 1H), 7.5(s,4H), 7.3(d,J=9.0, 1H), 4.9(d,J=6.0, 2H), 2.7(s,3H).

EXAMPLE 48

3-Acetyl-6,8-dichloro-4-(2-methylchclohexylamino)-2-quinolinone (311)

3-Acetyl-6,8-dichloro-4-methylsulfoxy-2-quinolinone (3.18g, 0.01 mol) and 2-methylcyclohexylamine (1.13g, 0.01 mol) were used, but the reaction was carried out as above process of example 37 to obtain the desired product (2.68g, yield: 73%).

$^1$H NMR (CDCl3): δ12.0(m,1H), 8.2(d,J=2.0, 1H), 7.9(brs, 1H), 7.6(d,J=2.0, 1H), 3.0(m,1H), 2.8(s,3H), 1.0~2.5(m,9H), 1.0~1.2(m,3H).

EXAMPLE 49

3-Acetyl-7-t-butyl-4-cyclobutylamino-2-quinolinone (377)

3-Acetyl-7-t-butyl-4-methylsulfoxy-2-methylsulfoxy-2-quinolinone (3.05g, 0.01 mol) and cyclobutylamine (0.71g, 0.01 mol) were used, but the reaction was carried out as the above process of example 37 to obtain the desired product (2.6g, yield: 83 %).

$^1$H NMR (CDCl3): δ11.4(m,1H), 8.3~8.4(d,1H), 7.2~7.7(m,2H), 2.9(s,3H), 1.5~2.9(m,4H), 1.2(s,9H), 0.9~1.1(m,2H).

EXAMPLE 50

3-Acetyl-8-ethyl-4-cyclopentylamino-2-quinolinone (400)

3-Acetyl-8-ethyl-4-methylsulfoxy-2-quinolinone (2.77g, 0.01 mol) and cyclopentylamine (0.86g, 0.01 mol) were used, but the reaction was carried out as the above process of example 37 to obtain the desired product (2.15g, yield: 72%).

$^1$H NMR (CDCl3): δ11.6(m,1H), 8.1(d,J=6.0, 1H), 7.4~7.1(m,3H), 3.8(m,1H), 2.8(s,3H), 2.7(m,2H), 2.1~1.5(m,8H), 1.4(t,J=6.0, 3H).

EXAMPLE 51

3-Acetyl-6-chloro-8-methyl-4-(p-fluorophenethylamino)-2-quinolinone (420)

3-Acetyl-6-chloro-8-methyl-4 -methylsulfoxy -2-quinolinone (2.98 g, 0.01 mol) and p-fluorophenethylamine hydrochloride (1.76g, 0.01 mol) were used, but the reaction was carried out as the above process of example 42 to obtain the desired product (2.9g, yield: 71%).

$^1$H NMR (DMSO-d6): δ11.5(m,1H), 8.3(s,1H), 7.9(s,1H), 7.6~6.8(m,5H), 3.77(m,2H), 3.0(t,J=7.0, 2H), 2.6(s,3H), 2.4(s,3H).

EXAMPLE 52

3-Acetyl-5,8-dichloro-4-(N-morpholino)-2-quinolinone (513)

3-Acetyl-5,8-dichloro-4-methylsulfoxy-2-quinolinone (3.18g, 0.01 mol) and morpholine (0.87 g, 0.01 mol) were used, but the reaction was carried out as the above process of example 37 to obtain the desired product (2.56g, yield: 75%).

$^1$H NMR (DMSO-d6): δ6.7~7.3(m,3H), 2.9~3.3(m, 8H), 2.3(s,3H).

EXAMPLE 53

3-Acetyl-5,7-dimethyl-4-(β-methylphenethylamino))-2-quinolinone (533)

3-Acetyl-5,7-dimethyl-4-methylsulfoxy-2-quinolinone (2.77g, 0.01 mol)and β-methylphenethylamine (1.35g, 0.01 mol) were used, but the reaction was carried out as the above process of example 37 to obtain hhe desired product (2.96g, yield: 85%).

$^1$H NMR (DMSO-d6): δ11.6(m,1H), 7.2(s,5H), 6.7~7.1 (d,2H), 3.5(m,2H), 3.2(m,1H), 2.7(s,3H), 2.6(s,3H), 2.2(s, 3H), 1.3(d,3H).

EXAMPLE 54

3-Acetyl-4-sec-butylamino-8-isopropyl-2-quinolinone (543)

3-Acetyl-4-methylsulfoxy-8-isopropyl-2-quinolinone (2.91g, 0.01 mol) and sec-butylamine (0.73g, 0.01 mol) were used, but the reaction was carried out as the above process of example 37 to obtain the desired product (2.7g, yield: 90%).

$^1$H NMR (CDCl3): δ11.6(m,1H), 8.2(d,J=8.0, 1H), 7.7~7.1(m,3H), 3.5(m,1H), 2.9(m,1H), 2.8(s,3H), 1.7(m,2H), 1.4(m,9H), 1.1(t,J=6.0, 3H).

EXAMPLE 55

3-Acetyl-4-(β-methylphenethylamino)-8-phenyl-2-quinolinone (565)

3-Acetyl-4-methylsulfoxy-8-phenyl-2-quinolinone (3.25g, 0.01 mol) and β-methylphenethylamine (1.35g, 0.01 mol) were used, but the reaction was carried out as the above process of example 37 to obtain the desired product (3.29g, yield: 83%).

$^1$H NMR (DMSO-d6): δ11.3(m,1H), 8.3(brs, 1H), 8.3~8.0(m,1H), 7.8~6.9(m,12H), 3.3(m,2H), 3.03(m,1H), 2.6(s,3H), 1.23(d,J=7.0, 3H).

EXAMPLE 56

3-Acetyl-4-allylamino-8-propyl-2-quinolinone (603)

3-Acetyl-4-allylamino-8-propyl-2-quinolinone (2.91g, 0.01 mol) and allylamine (0.57g, 0.01 mol) were used, but the reaction was carried out as the above process of example 37 to obtain the desired product (2.31g, yield: 75%).

$^1$H NMR (CDCl3): δ11.6(m,1H), 8.1(d,J=8.0, 1H), 7.7~7.1(m,3H), 6.0~5.3(m,3H), 4.1(brs,2H), 2.8(s,3H), 2.6(t,J=7.0, 2H), 1.5(m,2H), 1.0(t,J=6.0, 3H).

EXAMPLE 57

3-Acetyl-4-allylamino-8-chloro-6-methyl-2-quinolinone (611)

3-Acetyl-8-chloro-6-methyl-4 -methylsulfoxy -2-quinolinone (2.97 g, 0.01 mol) and allylamine (0.57g, 0.01 mol) were used, but the reaction was carried out as the above process of example 37 to obtain the desired product (2.38g, yield: 82%).

$^1$H NMR (DMSO-d6): δ11.6(m,1H), 8.2(s,1H), 7.4~7.7(d,2H), 5.0~6.1 (m,3H), 3.1 (t,2H), 2.5(s,3H), 2.2(s,3H).

EXAMPLE 58

3-Acetyl-4-allylamino-5-chloro-6-methyl-2-quinolinone (632)

3-Acetyl-5-chloro-6-methyl-4-methylsulfoxy-2-quinolinone (2.69g, 0.01 mol) and allylaminc (0.57g, 0.01 mol) were used, but the reaction was carried out as the above process of example 37 to obtain the desired product (2.23g, yield: 77%).

$^1$NMR (CDCl3): δ11.4(m,1H), 7.1~7.6(m,3H), 5.1~6.2(m,3H), 4.0~4.2(m,2H), 2.6(s,3H), 2.4(s,3H).

EXAMPLE 59

3-Acetyl-8-chloro-4-(p-chlorophenethylamino-5-methyl-2-quinolinone (656)

3-Acetyl-8-chloro-5-methyl-4-methylsulfoxy-2-quinolinone (2.97 g, 0.01 mol) and p-chlorophenethylamine (1.56g, 0.01 mol) were used, but the reaction was carried out as the above process of example 37 to obtain the desired product (3.1 lg, yield: 80%).

$^1$H NMR (DMSO-d$_6$): $\delta$11.6(m,1H), 8.7(s,1H), 7.7(s,4H), 7.1~7.9(m,2H), 3.9(q,2H), 3.2(t,2H), 2.9(s,3H), 2.7(s,3H).

EXAMPLE 60

3-Acetyl-4-isoamylamino-6-fluoro-8-chloro-2-quinolinone (673)

3-Acetyl-8-chloro-6-fluoro-4-methylsulfoxy-2-quinolinone (3.02g, 0.01 mol) and isoamylamine (0.87g, 0.01 mol) were used, but the reaction was carried out as the above process of example 37 to obtain the desired product (2.79g, yield: 86%).

$^1$H NMR (CDCl$_3$): $\delta$11.6(m,1H), 8.0~7.8(m,2H), 7.4(dd, J=8.0, 2.0, 1H), 3.4(m,2H), 2.8(s,3H), 1.7(m,3H), 0.9(d,J=6.0, 6H).

EXAMPLE 61

3-Acetyl-4-isobutylamino-5-trifluoromethyl-8-methoxy-2-quinolinone (682)

3-Acetyl-5-trifluoromehyl-8-methoxy-4-methylsulfoxy-2-quinolinone (3.4 7g, 0.01 mol) and isobutylamine (0.73g, 0.01 mol) were used, but the reaction was carried out as the above process of example 37 to obtain the desired product (2.46g, yield: 69%).

$^1$H NMR (DMSO-d$_6$): $\delta$11.1(m,1H), 8.5(brs,1H), 7.2~7.7(m,2H), 4.2(s,3H), 3.0~3.6(m,2H), 2.6(s,3H), 1.8~2.3(m,1H), 1.1 (d,J=6.0, 6H).

The fungicidal activities of 2-quinolinone derivatives(I) according to the present invention prepared by the above examples were tested by following Tests; wherein all the test chemicals were readily dispersed in a standard formulation of acetone in water and surfactant. Five ml of acetone containing 12.5 mg of the chemical was diluted in 45 ml of Tween 20 solution (250 ppm). Fifty ml of this chemical solution was sprayed to plants on the ramtable at the same time. All replicates of plants tested for fungicidal activity against 6 plant diseases were two pots, respectively.

TEST 1

Fungicidal Test for Rice Blast (RCB )

Evaluation of activity against blast was done with rice plants in the 2 leaf stage, grown in 5 cm pots with a foliage spray. Fifty ml test material was sprayed on the foliage. After the spray deposit had dried, the plants were inoculated with a suspension of conidia in water ($1 \times 10^6$ spores/ml) and placed in a dew chamber at 25° C. for 24 hrs. For inoculum preparation, rice blast fungus was incubated on rice polish agar medium at 26° C. for 2 weeks, and then scratched airial mycelia with rubber and irradiated with near UV light for 2 days. The plants were then held in lighted gowth chamber (26°±2° C., 85%) for an additional 5 days, and rated on the disease severity.

TEST 2

Fungicidal Test for Rice Sheath Blast (RSB)

Rice plants in the 3 leaf stage were sprayed with 5 ml of chemical solution on the turntable. One day after drying, treated plants were inoculated by injecting inoculum, incubated in wileat bran medium at 25° C. for 7 days, macerated into the mixer at the base of the rice plants. Those were moved to a lighted dew chamber at 28° C.and then held for 5 days. The disease severity of each pot was examined and compared to the standard rating diagram.

TEST 3

Fungicidal Test for Cucumber Gray Mold (CGM)

Cucumber plants grown in the fast leaf stage were sprayed with 50 ml of chemical solution while those were rotated on the mintable. After the spray deposit had dried for one day, the treated foliage of cucumber was inoculated with conidia ($1 \times 10^6$ spores/ml) of B. cinerea incubated on potato dextrose agar medium at 25° C. for 15 days by leaf spray all tour sides of plants until just before runoff and then placed in 20° C. dew chamber for 4~5 days. The disease rating was made by examining the applied plants and comparing the percent disease on a leaf to the standard rating diagram.

TEST 4

Fungicidal Test for Tomato Late Blight (TLB)

Tests were made onto tomato plants grown in 5 cm polyvinyl pots for 14 days by leaf spray. The foliage is sprayed to run off with a test chemical while the plant rotated on a turntable. After the spray deposit dried for one day, the treated plants were inoculated by spraying then with a suspension of zoosporangia ($1 \times 10^5$ zoosporangia/ml) incubated on V-8 juice agar medium at 20° C. for 2 weeks and then placed in a dew chamber at 18° C. for 48 hrs. Four days after inoculation, disease ratings were made on a investigation of the disease severity.

TEST 5

Fungicidal Test for Wheat Leaf Rust (WLR)

Tests were made on wheats (cultivar; Chokwang) grown in polyvinyl pots (diameter; 5 cm) for 7 days by foliage spray. The first leaf was sprayed while plaints were rotating on a turntable with 5 ml of a chemical solution. After the spray deposit dried, plants were dusted with a uredospores colonied on the second leaf of wheat and placed in a moist chamber at 20° C. for 24 hours. One day after inoculation, plant were moved to the plant growth chamber (20° C., 70% RH) for inducing the disease. The fungicidal effect of the applied chemicals was investigated on the disease severity of wheats after 10 days.

TEST 6

Fungicidal Test for Barley Powdery Mildew (BPM)

The barley powdery mildew is an obligately parasitic fungus that must be transferred directly from infected plants to healthy plants in a relatively dry environment. The host plants (cultivar; Allbori) sowed in polyvinyl pot(diameter; 5 cm) were grown in a greenhouse for 7 days. Healthy young barley with fully expanded primary leaf was spray with a suspension of a test material. One day after drying, the applied plants were dusted with conidia of *Erysiphe graminis* formed on the primary leaf of barley. The inoculated plants were placed in a plant growth chamber at 22°~24° C. and then induced the powdery mildew. The disease severity was rated after 7 day inoculation.

Fungicidal activity of test chemical against the above 6 plant diseases was indicated with control value calculated by below formula to list the result as below Table 4.

Control value(%) =

$$\left(1 - \frac{\text{Percent of disease area in treatment}}{\text{Percent of disease area in untreated control}}\right) \times 100$$

TABLE 4

| Comp. No. | Fungicidal effects for 2-quinolinone ||||||
| | RCB | RSB | CGM | TLB | WLR | BPM |
| --- | --- | --- | --- | --- | --- | --- |
| 13 | 100 | 80 | — | — | 100 | 58 |
| 18 | 97 | — | — | — | — | — |
| 19 | 84 | 65 | — | 97 | — | — |
| 33 | 96 | — | — | — | 100 | 100 |
| 34 | 89 | — | — | — | 100 | 84 |
| 35 | 100 | 100 | — | — | — | — |
| 38 | 96 | 68 | — | — | 100 | — |
| 39 | 14 | 45 | 99 | 94 | 29 | 28 |
| 49 | 95 | 74 | 42 | 78 | 99 | 49 |
| 55 | 0 | 32 | 92 | 0 | 0 | 51 |
| 75 | 100 | 100 | 0 | 0 | 99 | 75 |
| 106 | 99 | 95 | 57 | 100 | 53 | 10 |
| 107 | 94 | 20 | 93 | 99 | 60 | 9 |
| 108 | 97 | 67 | 95 | 100 | 53 | 9 |
| 111 | 99 | 95 | 95 | 97 | 53 | 10 |
| 112 | 99 | 95 | 95 | 97 | 53 | 16 |
| 118 | 0 | 30 | 90 | 56 | 0 | 0 |
| 120 | 91 | 60 | 95 | 92 | 53 | 0 |
| 129 | 0 | 37 | 98 | 38 | 0 | 0 |
| 131 | 0 | 16 | 99 | 47 | 53 | 23 |
| 137 | 96 | 53 | 94 | 94 | 27 | 0 |
| 152 | 99 | 95 | 89 | 60 | 33 | 58 |
| 159 | 93 | 90 | 66 | 0 | 91 | 69 |
| 165 | 99 | 90 | 83 | 31 | 67 | 0 |
| 176 | 99 | 32 | 38 | 73 | 0 | 0 |
| 181 | 99 | 63 | 31 | 57 | 75 | 95 |
| 183 | 94 | 74 | 0 | 50 | 75 | 18 |
| 189 | 94 | 100 | 0 | 0 | 100 | 100 |
| 190 | 86 | 90 | 91 | 62 | 45 | 0 |
| 191 | 100 | 85 | 42 | 30 | 10 | 33 |
| 192 | 100 | 90 | 100 | 18 | 43 | 95 |
| 193 | 100 | 95 | 40 | 70 | 100 | 70 |
| 194 | 99 | 99 | 81 | 20 | 100 | 55 |
| 195 | 100 | 99 | 100 | 0 | 99 | 56 |
| 196 | 100 | 86 | 45 | 100 | 42 | 0 |
| 197 | 99 | 92 | 0 | 7 | 100 | 83 |
| 199 | 99 | 52 | 73 | 61 | 8 | 53 |
| 200 | 96 | 52 | 21 | 72 | 56 | 4 |
| 204 | 72 | 81 | 0 | 0 | 100 | 100 |
| 205 | 100 | 21 | 76 | 98 | 81 | 54 |
| 206 | 100 | 91 | 61 | 0 | 100 | 71 |
| 211 | 100 | 75 | 21 | 92 | 38 | 8 |
| 215 | 84 | 13 | 19 | 0 | 67 | 97 |
| 219 | 0 | 20 | 95 | 6 | 53 | 0 |
| 222 | 91 | 26 | 69 | 24 | 27 | 0 |
| 224 | 100 | 100 | — | — | 67 | 89 |
| 226 | 100 | — | — | 48 | — | — |
| 228 | 99 | — | — | 91 | — | — |
| 231 | 100 | — | — | — | — | 97 |
| 235 | 87 | 11 | — | 89 | — | — |
| 236 | 100 | 100 | 35 | 89 | — | — |
| 237 | — | 69 | — | 93 | 93 | — |
| 238 | — | 100 | — | 47 | 98 | — |
| 239 | — | — | — | 89 | — | — |
| 242 | 100 | 100 | 100 | — | 93 | 76 |
| 247 | 97 | — | — | 96 | — | — |
| 251 | 100 | 100 | — | — | 96 | — |
| 253 | — | — | 94 | — | — | — |
| 257 | — | — | 77 | 95 | — | — |
| 259 | 99 | — | — | — | — | — |

TABLE 4-continued

| Comp. No. | Fungicidal effects for 2-quinolinone ||||||
| | RCB | RSB | CGM | TLB | WLR | BPM |
| --- | --- | --- | --- | --- | --- | --- |
| 267 | 71 | — | 95 | 35 | 14 | 42 |
| 268 | 0 | 0 | 92 | 19 | 0 | 53 |
| 272 | 100 | — | 66 | 100 | — | — |
| 279 | 99 | 35 | 68 | 87 | 53 | 2 |
| 282 | 7 | 0 | 98 | 97 | 0 | 35 |
| 308 | 0 | 53 | 15 | 98 | — | — |
| 310 | 0 | 13 | 90 | 37 | 27 | 31 |
| 313 | 98 | 53 | 58 | 95 | 60 | 11 |
| 336 | 0 | 0 | 100 | 21 | 0 | 13 |
| 368 | 18 | 0 | 93 | 0 | 0 | 2 |
| 404 | 0 | 0 | 59 | 0 | 99 | 100 |
| 407 | 57 | 0 | 38 | 95 | 67 | 29 |
| 435 | 93 | 71 | 48 | 91 | 93 | 0 |
| 475 | 0 | 10 | 95 | 48 | 67 | 43 |
| 476 | 0 | 95 | 67 | 11 | 0 | 61 |
| 506 | 0 | 35 | 94 | 65 | 0 | 0 |
| 540 | 0 | 20 | 94 | 55 | 0 | 0 |
| 542 | 0 | 30 | 94 | 84 | 0 | 0 |
| 545 | 0 | 95 | 42 | 82 | 53 | 1 |
| 550 | 0 | 58 | 97 | 63 | 0 | 0 |
| 608 | 7 | 75 | 82 | 93 | 9 | 0 |
| 609 | 0 | 15 | 92 | 21 | 0 | 0 |
| 708 | 93 | 28 | 68 | 46 | 0 | 0 |
| 709 | 14 | 28 | 92 | 3 | 0 | 0 |
| 711 | 0 | 50 | 94 | 13 | 0 | 17 |
| 713 | 7 | 5 | 95 | 77 | 0 | 39 |
| 715 | 0 | 0 | 100 | 28 | 27 | 4 |
| 718 | 96 | 60 | 13 | 78 | 27 | 5 |
| 720 | 93 | 30 | 38 | 81 | 53 | 20 |
| 721 | 99 | 95 | 59 | 83 | 80 | 5 |
| 736 | 100 | 100 | 60 | 71 | 53 | 19 |
| 737 | 98 | 80 | 0 | 76 | 82 | 14 |
| 745 | 0 | 5 | 92 | 59 | 0 | 16 |
| 746 | 0 | 30 | 94 | 71 | 0 | 0 |
| 759 | 0 | 10 | 96 | 76 | 0 | 46 |
| 761 | 99 | 95 | 0 | 60 | 53 | 95 |
| 765 | 0 | 11 | 95 | 36 | 0 | 0 |
| 791 | 93 | 61 | 40 | 46 | 0 | 17 |
| 792 | 98 | 11 | 81 | 94 | 27 | 29 |
| 793 | 91 | 15 | 100 | 47 | 53 | 45 |
| 797 | 99 | 60 | 100 | 96 | 53 | 4 |
| 798 | 97 | 20 | 13 | 35 | 27 | 32 |
| 801 | 99 | 70 | 0 | 65 | 75 | 31 |
| 802 | 98 | 70 | 72 | 79 | 68 | 42 |
| 803 | 100 | 95 | 99 | 50 | 67 | 24 |
| 804 | 99 | 68 | 100 | 29 | 53 | 58 |
| 805 | 100 | 95 | 80 | 57 | 60 | 61 |
| 806 | 100 | 79 | 56 | 36 | 27 | 14 |
| 807 | 99 | 95 | 69 | 57 | 53 | 0 |
| 808 | 99 | 95 | 50 | 43 | 53 | 10 |
| 809 | 99 | 58 | 71 | 53 | 60 | 2 |
| 810 | 99 | 21 | 81 | 73 | 53 | 24 |
| 813 | 99 | 37 | 56 | 24 | 33 | 14 |
| 830 | 0 | 0 | 93 | 23 | 0 | 20 |
| 831 | 0 | 0 | 100 | 46 | 0 | 15 |
| 837 | 96 | 60 | 72 | 81 | 36 | 0 |
| 839 | 0 | 35 | 96 | 87 | 45 | 15 |
| 841 | 57 | 90 | 91 | 86 | 77 | 9 |
| 846 | 0 | 0 | 98 | 77 | 0 | 0 |
| 853 | 91 | 85 | 78 | 15 | 0 | 98 |
| 862 | 99 | 5 | 77 | 0 | 27 | 36 |
| 869 | 0 | 100 | 24 | 0 | 96 | 95 |
| 870 | 100 | 83 | 3 | 56 | 87 | 0 |
| 871 | 100 | 63 | 12 | 73 | 92 | 33 |
| 876 | 97 | 33 | 21 | 53 | 81 | 62 |
| 877 | 100 | 8 | 15 | 62 | 63 | 53 |
| 878 | 100 | 96 | 24 | 0 | 82 | 18 |
| 905 | 26 | 0 | 0 | 98 | 96 | 23 |
| 908 | 0 | 0 | 0 | 95 | 64 | 5 |
| 915 | 100 | 82 | 28 | 85 | 81 | 23 |
| 916 | 100 | 82 | 36 | 81 | 76 | 15 |
| 928 | 23 | 75 | 67 | 25 | 99 | 61 |
| 929 | 90 | 90 | 63 | 0 | 100 | 92 |
| 932 | 86 | 95 | 20 | 15 | 96 | 91 |
| 933 | 100 | 75 | 40 | 0 | 33 | 70 |
| 936 | 100 | 35 | 7 | 25 | 91 | 46 |
| 937 | 100 | 15 | 64 | 32 | 27 | 39 |
| 939 | 100 | 35 | 14 | 96 | 27 | 81 |
| 944 | 50 | 85 | 0 | 0 | 96 | 99 |

TABLE 4-continued

| Comp. No. | Fungicidal effects for 2-quinolinone | | | | | |
|---|---|---|---|---|---|---|
| | RCB | RSB | CGM | TLB | WLR | BPM |
| 946 | 14 | 90 | 0 | 0 | 100 | 99 |
| 947 | 21 | 0 | 24 | 0 | 100 | 97 |
| 949 | 94 | 60 | 23 | 0 | 53 | 97 |

As the result of the above Table 4, the com pounds according to the present invention have a high protective effect against CGM and TLB, and also RCB.

The insecticidal activity of the compounds of the formula(I) according to the present invention was tested as following Tests 7~10.

The Primary Screening(PRI) is designed to detect initial pest control activity of experimental compounds. The types of activity assayed are acute toxicity, and growth disruption. The bioassay are designed to detect contact and ingestion activity.

The stage tested are as follows: adult brown planthopper(BPH), green peach aphid(GPA), and two-spotted spider mite (TSSM), and 3rd instar diamondback moth(DBM).

All experimental compounds are formulated in a 10: 90 (acetone: water), Triton X-100 100ppm solution at a single, unreplicated rate of 500 ppm. Formulated compounds are applied to the test species with the individual application methods respectively.

TEST 7

Insecticidal Test for Brown Plant Hopper (BPH)

Root parts of six rice seddlings (cultivar: Dongjin; 5–6 cm in length; 5–10 day old) are rolled with cotton wool pads and rice seedlings are put into the glass test robes($\phi 3 \times 15$ cm) containing 2 ml water. Three to five day-old adult BPH (20 individuals) are collected from rearing cages by an aspirator, and placed into test robes.

Test chemicals are dissolved in 5 ml acetone(100%), and formulated to the proper concentration in Triton X-100 (100ppm), then sprayed onto the BPH directly. The test tubes are covered with nylon cloth and held in an incubator at 25° C. Insect mortalities are recorded at 24 and 48 hours after treatment.

TEST 8

Insecticidal Test for Green Peach Aphid (GPA)

Excised tobacco leaf disks (5.5 cm in diameter) are dipped into the prepared test chemical solutions (30 sec) and taken out. After drying (30 min), leaf disks are placed in the petridishes ($\phi 5.5 \times 2$ cm) and apterous female adult GPAs (20 individuals) are enclosed. All petridishes are covered and held in an incubator at 25° C. Insect mortalities are recorded at 24 and 48 hours after treatment.

TEST 9

Insecticidal Test for Two-Spotted Spider Mite (TSSM)

Excised kidney bean leaf disks (2.5 cm in diameter) are placed on water saturated cotton wool pads fitted into petridishes ($\phi 5.5 \times 2$ cm). Female adult TSSMs (30 individuals) are placed on leaf disks, and prepared test chemicals are sprayed. The petridishes are covered and held in an incubator at 25° C. Mite mortalities are recorded at 24 and 48 hours after teatment.

TEST 10

Insecticidal Test for Diamond-Back Moth (DBM)

Test chemicals axe dissolved in 5ml acetone (100%), then formulated to the proper concentration in Triton X- 100 ( 100 ppm). Excised cabbage leaf disks(5 cm in diameter) are dipped into the solution (30 sec) and taken out. After drying (30 min), leaf disks are placed in the petridishes ($\phi 5 \times 1$ cm) and 3rd instar DBM larvae (10 individuals) are enclosed. All petridshes are covered and held in an incubator at 25° C. Insect mortalities are recorded at 24 and 48 hours after treatment.

The mortality (%) of test chemical against the above plant diseases was calculated by the below fomula to list the result as the following Table 5.

$$\text{Mortality}(\%) = \frac{\text{No. of dead insects}}{\text{No. of treated insects}} \times 100$$

TABLE 5

| Comp. No. | Insecticidal effects for 2-quinolinone (I) | | | |
|---|---|---|---|---|
| | BPH | GPA | DBM | TSSM |
| 13 | — | — | — | 100 |
| 28 | — | — | 90 | — |
| 29 | 20 | 0 | 90 | 100 |
| 30 | 10 | 0 | 20 | 100 |
| 33 | 0 | 25 | 40 | 100 |
| 34 | 5 | 75 | 60 | 100 |
| 38 | 0 | 30 | 80 | 100 |
| 224 | 10 | 0 | 100 | 63 |
| 241 | 0 | 0 | 100 | 0 |
| 242 | 0 | 0 | 80 | 100 |
| 245 | 0 | 0 | 90 | 100 |
| 307 | 0 | 10 | 100 | 7 |
| 404 | 0 | 0 | 100 | 100 |
| 460 | 0 | 0 | 100 | 0 |

As the result of the above Table 5, the compounds of the formula(I) according to the present invention have selectively good activity against diamond-back moth and two-spotted spider mite.

What is claimed is:

1. 2-Quinolinone derivatives having the following formula (I)

wherein, $R_1$, $R_2$, $R_3$ and $R_4$ are independently hydrogen, halogen, $C_1$–$C_{10}$ alkyl, $C_1$–$C_3$ haloalkyl, $C_1$–$C_8$ alkoxy, $C_1$–$C_3$ alkylthio, $C_1$–$C_3$ haloalkylthio, $NO_2$, $CN$, alkoxy carbonyl, phenyl, phenoxy, benzenesulfonyl, benzyl, or morpholine;

$R_5$ is $C_1$–$C_6$ alkyl, $C_3$–$C_6$ cycloalkyl, phenyl, benzyl or phenylthio methyl; and X is $S(O)nR_6$, $OR_9$ or NAB;

wherein, n is 0 or 1;

$R_6$ is $R_7$ or $R_8$, and $R_7$ is $C_1$–$C_6$ alkyl, $C_1$–$C_3$ haloalkyl, benzyl or benzyl substituted with a $C_1$–$C_4$ alkyl, $C_1$–$C_3$ alkoxy, one or two halogen groups, or trifluoromethyl, and $R_8$ is phenyl, phenyl substituted with a halogen, or benzyl;

$R_9$ is $C_2$-$C_5$ alkyl, $C_5$-$C_6$ cycloalkyl, phenyl or phenyl substituted with a halogen;

A and B are combined together with the nitrogen atom to form a saturated or unsaturated 5 or 6-membered cyclic ring or benzofused 5- or 6-membered cyclic ring, or a saturated or unsaturated 5 or 6-membered cyclic ring including an additional hetero atom selected from O or N, or a saturated or unsaturated 5 of 6-membered cyclic ring, substituted with $C_1$-$C_3$ alkyl, or one of A and B is H and the other is $R_{10}$ or Z—Ar;

and then, $R_{10}$ is saturated $C_1$-$C_{10}$ alkyl, propenyl, $C_3$-$C_6$ cycloalkyl which includes a hetero atom selected from O, S or N or $C_3$-$C_6$ cycloalkyl substituted with $C_1$-$C_3$ alkyl or alkoxycarbonyl, $C_1$-$C_3$ haloalkyl, alkoxyalkyl, alkoxycarbonylalkyl, Ar, pyridyl, pyridyl substituted with a halogen, one or two $C_1$-$C_3$ alkyl groups, or $C_1$-$C_3$ alkoxy, pyrimidyl or pyrimidyl substituted by one or two $C_1$-$C_3$alkyl, $C_1$-$C_3$ alkoxy, or one or two $C_1$-$C_3$ alkyl and $C_1$-$C_3$ alkoxy;

Z is $C_1$-$C_4$ alkyl chain, $C_1$-$C_4$ alkyl chain containing cyclopropylene ring, or $C_1$-$C_4$ alkyl chain substituted with $C_1$-$C_3$ alkyl, $C_1$-$C_3$ alkoxy, $C_1$-$C_3$ hydroxyalkyl or phenyl; and Ar is $C_3$-$C_6$ cycloalkyl, $C_3$-$C_6$ cycloalkyl including a nitrogen atom, or pyridyl, or a phenyl group of the following formula(II)

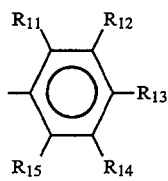

wherein, $R_{11}$, $R_{12}$, $R_{13}$, $R_{14}$ and R15 are independently H, halogen, $C_1$-$C_6$ alkyl, $C_1$-$C_4$ haloalkyl, $C_1$-$C_4$ alkoxy, phenyl, phenoxy, phenylthio, CN, $NO_2$, $NH_2$, or $SO_2NH_2$.

2. Fungicides including a fungicidal effective amount of 2-quinolinone derivatives having the following formula (I) as an effective ingredient

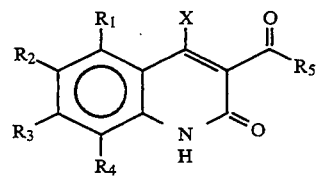

wherein, $R_1$, $R_2$, $R_3$, $R_4$, $R_5$ and X are as defined in the above claim 1.

3. Insecticides including an insecticidal effective amount of 2-quinolinone derivatives having the following formula (I) as an effective ingredient

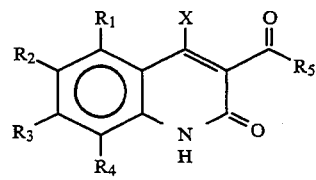

wherein, $R_1$, $R_2$, $R_3$, $R_4$, $R_5$ and X are as defined in the above claim 1.

4. A process for preparing 2-quinolinone derivatives of the following formula(Ia) by thermally cyclizing ketenedithioacetal α-anilide of the following formula(HI).

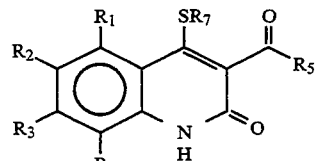

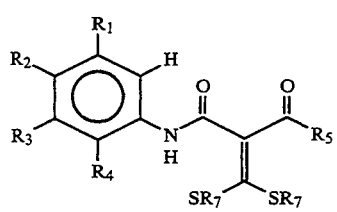

wherein, $R_1$, $R_2$, $R_3$, $R_4$, $R_5$ and $R_7$ are respectively as defined in the above claim 1.

* * * * *